United States Patent [19]

Hunkeler et al.

[11] Patent Number: 4,775,671

[45] Date of Patent: Oct. 4, 1988

[54] IMIDAZODIAZEPINES

[75] Inventors: Walter Hunkeler, Magden; Emilio Kyburz, Reinach, both of Switzerland

[73] Assignee: Hoffmann-La Roche Inc., Nutley, N.J.

[21] Appl. No.: 122,106

[22] Filed: Nov. 18, 1987

Related U.S. Application Data

[63] Continuation of Ser. No. 691,297, Jan. 14, 1985, abandoned.

[30] Foreign Application Priority Data

Jan. 19, 1984 [CH] Switzerland ............................ 225/84
Jun. 29, 1984 [CH] Switzerland ......................... 3149/84
Oct. 26, 1984 [CH] Switzerland ......................... 5123/84

[51] Int. Cl.[4] .................... A61K 31/55; C07D 487/14; C07D 487/04; C07D 495/14
[52] U.S. Cl. .................... 514/220; 540/498; 540/503; 540/495; 540/506; 540/511; 540/504
[58] Field of Search .................... 514/220; 540/498

[56] References Cited

U.S. PATENT DOCUMENTS

| | | | |
|---|---|---|---|
| 4,031,079 | 6/1977 | Mohrbacher et al. | 540/514 |
| 4,316,839 | 2/1982 | Gereke et al. | 514/220 |
| 4,352,815 | 10/1982 | Hunkeler et al. | 514/220 |
| 4,352,816 | 10/1982 | Hunkeler et al. | 514/220 |
| 4,352,817 | 10/1982 | Hunkeler et al. | 514/220 |
| 4,352,818 | 10/1982 | Hunkeler et al. | 514/220 |
| 4,353,827 | 10/1982 | Hunkeler et al. | 540/498 |
| 4,359,420 | 6/1982 | Gereke et al. | 514/220 |
| 4,362,732 | 12/1982 | Hunkeler et al. | 514/220 |
| 4,435,403 | 3/1984 | Braestrup et al. | 546/86 |
| 4,489,003 | 12/1984 | Hunkeler et al. | 540/498 |
| 4,507,313 | 3/1985 | Braestrup et al. | 514/220 |
| 4,622,320 | 11/1986 | Watjen et al. | 514/220 |
| 4,622,321 | 11/1986 | Watjen et al. | 514/220 |

FOREIGN PATENT DOCUMENTS

| | | | |
|---|---|---|---|
| 0005102 | 11/1982 | Denmark | 540/498 |
| 0054507 | 6/1982 | European Pat. Off. | 540/514 |
| 0109921 | 5/1984 | European Pat. Off. | 514/220 |
| 0197282 | 10/1986 | European Pat. Off. | 514/220 |

OTHER PUBLICATIONS

R. F. Squires and C. Braestrup "Benzodiazepine Receptors in Rat Brain", Nature, vol. 266, pp. 732–734, (1977).
Chang et al., "Benzodiazepine Receptors: Labeling in Intact Animals With [3]H Fluritrazepam", European Journal of Pharmacology, vol. 48, pp. 213–218, (1978).

*Primary Examiner*—Robert T. Bond
*Attorney, Agent, or Firm*—Jon S. Saxe; Bernard S. Leon; William G. Isgro

[57] ABSTRACT

There is presented compounds of the formula

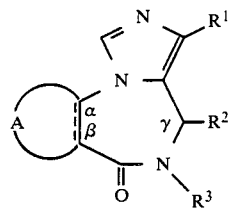

wherein A together with the two carbon atoms denoted by α and β signifies one of the groups

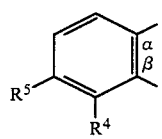

(1)

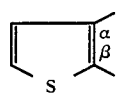

(2)

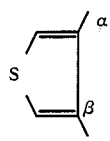

(3)

and

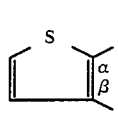

(4)

and the dotted line signifies the double bond present in cases (1), (2) and (4) and wherein $R^1$ signifies a 5- or 6-membered aromatic heterocyclic group or the group —$C(R^6)$=$NOR^7$(B), $R^2$ signifies hydrogen and $R^3$ signifies hydrogen or lower alkyl or $R^2$ and $R^3$ together signify dimethylene, trimethylene or propenylene, $R^4$ and $R^5$ each signify hydrogen, halogen, trifluoromethyl, cyano, nitro, amino or lower alkyl, $R^6$ signifies hydrogen or lower alkyl and $R^7$ signifies lower alkyl, the compound of formula I having the (S) or (R,S) configuration with reference to the carbon atom denoted by γ when $R^2$ and $R^3$ together signify dimethylene, trimethylene or propenylene, and pharmaceutically acceptable acid addition salts thereof have a pronounced affinity to the central benzodiazepine receptors and have anxiolytic, anticonvulsant, muscle relaxant and sedative-hypnotic properties.

26 Claims, No Drawings

IMIDAZODIAZEPINES

This is a continuation of application Ser. No. 691,297 filed Jan. 14, 1985, now abandoned.

DESCRIPTION OF THE INVENTION

The present invention is concerned with novel imidazodiazepine derivatives. In particular, it is concerned with imidazodiazepine derivatives of the general formula

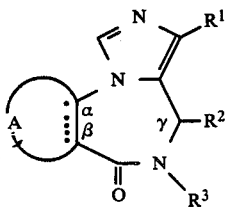

wherein A together with the two carbon atoms denoted by α and β signifies one of the groups

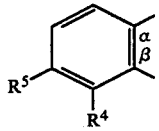

(1)

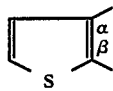

(2)

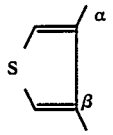

(3)

and

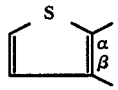

(4)

and the dotted line signifies the double bond present in cases (1), (2) and (4) and wherein $R^1$ signifies a 5- or 6-membered aromatic heterocyclic group or the group $—C(R^6)=NOR^7(B)$, $R^2$ signifies hydrogen and $R^3$ signifies hydrogen or lower alkyl or $R^2$ and $R^3$ together signify dimethylene, trimethylene or propenylene, $R^4$ and $R^5$ each signify hydrogen, halogen, trifluoromethyl, cyano, nitro, amino or lower alkyl, $R^6$ signifies hydrogen or lower alkyl and $R^7$ signifies lower alkyl, the compounds of formula I having the (S) or (R,S) configuration with reference to the carbon atoms denoted by γ and $R^2$ and $R^3$ together signify dimethylene, trimethylene or propylene, and pharmaceutically acceptable acid addition salts thereof, which have valuable pharmacodynamic properties.

Objects of the present invention are compounds of formula I above and pharmaceutically acceptable acid addition salts thereof per se and as pharmaceutically active substances, the manufacture of these compounds and intermediates of their manufacture, medicaments containing a compound of formula I or a pharmaceutically acceptable acid addition salt thereof, the manufacture of such medicaments and the use of the substances in accordance with the invention in the control or prevention of illnesses.

The term "lower alkyl" denotes residues and compounds with at most 7, preferably at most 4, carbon atoms. The terms "alkyl", "alkyl group" and the like denote straight-chain or branched, saturated hydrocarbon residues such as methyl, ethyl, n-propyl, isopropyl, n-butyl, s-butyl, t-butyl and the like. The term "cycloalkyl" denotes cyclic saturated hydrocarbon residues such as cyclopropyl and the like. The term "alkoxy" denotes alkyl groups attached via an oxygen atom such as e.g. methoxy, ethoxy, isopropoxy and the like. The term "alkoxyalkyl" denotes residues such as methoxymethyl and the like.

The term "5- or 6-membered aromatic heterocyclic group" denotes:

(a) a 5-membered, aromatic heterocyclic group which contains as a ring member an oxygen atom, a sulphur atom or the group $>NR^8$, in which $R^8$ signifies hydrogen or lower alkyl, and optionally a further one or two nitrogen atoms and which is attached via a carbon atom, preferably via a carbon atom adjacent to a hetero atom, for example a 2-oxazolyl, 4-oxazolyl, 5-oxazolyl, 3-isoxazolyl, 4-isoxazolyl, 5-isoxazolyl, 2-thiazolyl, 2-imidazolyl, 4-imidazolyl, 1,2,4-oxadiazol-3-yl, 1,2,4-oxadiazol-5-yl, 1,3,4-oxadiazol-2-yl, 1,2,5-oxadiazol-3-yl, 1,2,4-thiadiazol-3-yl, 1,3,4-thiadiazol-2-yl, 1,2,5-thiadiazol-3-yl or 1,2,4-triazol-3-yl group;

(b) a 5-membered, aromatic heterocyclic group which is attached via a nitrogen atom and which optionally contains as a ring member a further one or two additional nitrogen atoms, for example a 1-pyrrolyl, 1-imidazolyl, 1-pyrazolyl or 1,3,4-triazol-1-yl group; or (c) a 6-membered, aromatic heterocyclic group which contains as a ring member up to three nitrogen atoms and which is attached via a carbon atom, preferably via a carbon atom adjacent to a hetero atom, for example a 2-pyrimidinyl, 4-pyrimidinyl, 5-pyrimidinyl, 2-pyrazinyl, 4-pyridazinyl, 1,2,4-triazin-3-yl, 1,2,4-triazin-5-yl or 1,2,4-triazin-6-yl group.

These aromatic, heterocyclic groups can be unsubstituted or substituted on a carbon atom by lower alkyl, $(C_3-C_6)$-cycloalkyl, trifluoromethyl, phenyl, amino, lower alkylamino, lower alkoxy-lower alkyl or hydroxy, a keto-enol tautomerism being possible in the case of groups which are substituted by hydroxy.

$R^1$ preferably signifies the group $—C(R^6)=NOR^7$, in which $R^6$ preferably signifies hydrogen and $R^7$ signifies lower alkyl, or a 5-membered, aromatic heterocyclic group which contains as a ring member an oxygen atom or a sulphur atom and one or two nitrogen atoms and which is optionally substituted by lower alkyl, $(C_3-C_6)$-cycloalkyl or trifluoromethyl and which is preferably attached via a carbon atom which is adjacent to two hetero atoms.

In an especially preferred embodiment $R^1$ signifies a 1,2,4-oxadiazol-3-yl, 1,2,4-oxadiazol-5-yl or 1,3,4-oxadiazol-2-yl group which is optionally substituted by lower alkyl or $(C_3-C_6)$-cycloalkyl, with 3-methyl-1,2,4-oxadiazol-5-yl and 3-cyclopropyl-1,2,4-oxadiazol-5-yl being particularly preferred.

Preferably, $R^2$ signifies hydrogen and $R^3$ signifies lower alkyl or $R^2$ and $R^3$ together signify dimethylene or trimethylene. In an especially preferred embodiment R[2] and R[3] together signify dimethylene or trimethylene, the corresponding compounds of formula I having the (S) configuration with reference to the carbon atom denoted by γ.

When A signifies group (1), then R[4] preferably signifies hydrogen, halogen or trifluoromethyl and R[5] preferably signifies hydrogen or halogen.

A particularly preferred compound of general formula I is:

7-Chloro-3-(3-cyclopropyl-1,2,4-oxadiazol-5-yl)-5,6-dihydro-5-methyl-4H-imidazo[1,5-a][1,4]benzodiazepin-6-one.

Further especially preferred compounds of general formula I are:

(S)-8-Chloro-7-fluoro-11,12,13,13a-tetrahydro-1-(3-methyl-1,2,4-oxadiazol-5-yl)-9H-imidazo[1,5-a]pyrrolo-[2,1-c][1,4]benzodiazepin-9-one, (S)-8-bromo-11,12,13,13a-tetrahydo-1-(3-methyl-1,2,4-oxadiazol-5-yl)-9H-imidazo[1,5-a]pyrrolo[2,1-c][1,4]benzodiazepin-9-one, (S)-8-chloro-11,12,13,13a-tetrahydro-1-(3-methyl-1,2,4-oxadizol-5-yl)-9H-imidazo[1,5-a]pyrrolo[2,1-c][1,4]benzodiazepin-9-one, (S)-8-chloro-12,12a-dihydro-1-(3-methyl-1,2,4-oxadiazol-5-yl)-9H,11H-azeto[2,1-c]imidazo[1,5-a][1,4]benzodiazepin-9-one, (S)-12,12a-dihydro-1-(3-methyl-1,2,4-oxadiazol-5-yl)-8-(trifluoromethyl)-9H,11H-azeto[2,1-c]imidazo[1,5-a][1,4]benzodiazepin-9-one, (S)-8-chloro-1-(3-cyclopropyl-1,2,4-oxadiazol-5-yl)-12,12a-dihydro-9H,11H-azeto[2,1-c]imidazo[1,5-a][1,4]benzodiazepin-9-one, (S)-8-chloro-1-(3-cyclopropyl-1,2,4-oxadiazol-5-yl)-11,12,13,13a-tetrahydro-9H-imidazo[1,5-a]pyrrolo[2,1-c][1,4]benzodiazepin-9-one and 3-(3-cyclopropyl-1,2,4-oxadiazol-5-yl)-8-fluoro-5,6-dihydro-5-methyl-4H-imidazo[1,5-a][1,4]benzodiazepin-6-one.

Further preferred compounds of formula I in accordance with the invention are:

(R,S)-8-Chloro-12,12a-dihydro-1-(3-methyl-1,2,4-oxadiazol-5-yl)-9H,11H-azeto[2,1-c]imidazo[1,5-a][1,4]benzodiazepin-9-one, 8-fluoro-5,6-dihydro-5-methyl-3-(3-methyl-1,2,4-oxadiazol-5-yl)-4H-imidazo[1,5-a][1,4]benzodiazepin-6-one, 7-chloro-5,6-dihydro-5-methyl-3-(3-methyl-1,2,4-oxadiazol-5-yl)-4H-imidazo[1,5-a][1,4]benzodiazepin-6-one, (R,S)-7-fluoro-11,12,13,13a-tetrahydro-1-(3-methyl-1,2,4-oxadiazol-5-yl)-9H-imidazo[1,5-a]pyrrolo[2,1-c][1,4]benzodiazepin-9-one, (S)-8-chloro-11,12,13,13a-tetrahydro-1-(5-methyl-1,2,4-oxdiazol-3-yl)-9H-imidazo[1,5-a]pyrrolo[2,1-c][1,4]benzodiazepin-9-one, (S)-8-chloro-11,12,13,13a-tetrahydro-1-(3-isopropyl-1,2,4-oxadiazol-5-yl)-9H-imidazo[1,5-a]pyrrolo[2,1-c][1,4]benzodiazepin-9-one, (R,S)-8-chloro-12,12a-dihydro-1-(5-methyl-1,3,4-oxadiazol-2-yl)-9H,11H-azeto[2,1-c]imidazo[1,5-a][1,4]benzodiazepin-9-one, (S)-8-chloro-12,12a-dihydro-1-(1,3,4-oxadiazol-2-yl)-9H,11H-azeto[2,1-c]imidazo[1,5-a][1,4]benzodiazepin-9-one, (S)-8-chloro-11,12,13,13a-tetrahydro-1-(1,3,4-oxadiazol-2-yl)-9H-imidazo[1,5-a]pyrrolo[2,1-c][1,4]benzodiazepin-9-one, (S)-8-chloro-11,12,13,13a-tetrahydro-1-(5-methyl-1,3,4-oxadiazol-2-yl)-9H-imidazo[1,5-a]pyrrolo[2,1-c][1,4]benzodiazepin-9-one, (S)-8-chloro-1-(5-ethyl-1,3,4-oxadiazol-2-yl)-11,12,13,13a-tetrahydro-9H-imidazo[1,5-a]pyrrolo[2,1-c]benzodiazepin-9-one, (S)-8-chloro-12,12a-dihydro-9-oxo-9H,11H-azeto[2,1-c]imidazo[1,5-a][1,4]benzodiazepin-1-carboxaldehyde O-methyl oxime and (S)-8-chloro-11,12,13,13a-tetrahydro-1-[5-(trifluoromethyl)-1,2,4-oxadiazol-3-yl]-9H-imidazo[1,5-a]pyrrolo[2,1-c][1,4]benzodiazepin-9-one.

Apart from the compounds referenced to previously as being preferred, the invention is concerned in a particular embodiment with compounds of formula I, wherein R[1] signifies neither 1,2,4-oxadiazol-5-yl which is substituted in the 3-position by ($C_1$–$C_3$)-alkyl nor 1,2,4-oxadiazol-3-yl which is substituted in the 5-position by ($C_1$–$C_3$)-alkyl when A signifies the group (1), R[2] signifies hydrogen, R[3] signifies hydrogen or methyl, one of R[4] and R[5] signifies hydrogen and the other signifies hydrogen, chlorine, fluorine or nitro.

The compounds of formula I above and their pharmaceutically acceptable acid addition salts can be manufactured starting from compounds with are known per se and which have the general formulae

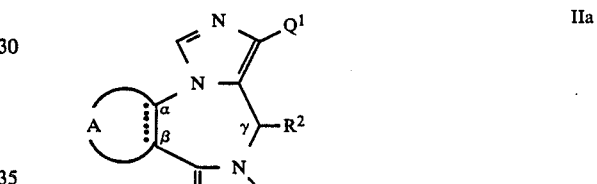

IIa

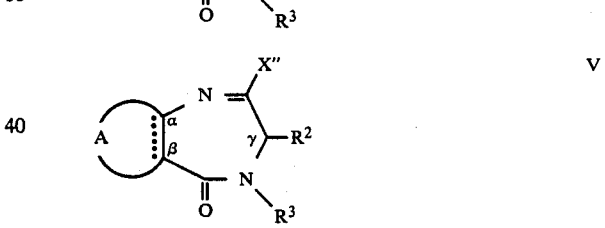

V wherein $Q^1$ signifies the group —$COR^6$, —$C(R^6)$=NOH, —C≡N, —$NH_2$, —CHO, —$CONH_2$ or —COX and X and X″ signify leaving groups and R[2], R[3], A and R[6] have the above significance, according to methods which are known per se and which are familiar to any person skilled in the art. The appropriate choice of the suitable starting materials, reagents and reaction conditions presents no difficulties to a person skilled in the art having regard to the desired compound of formula I.

In particular, compounds of formula I can be manufactured starting from compounds of the general formula

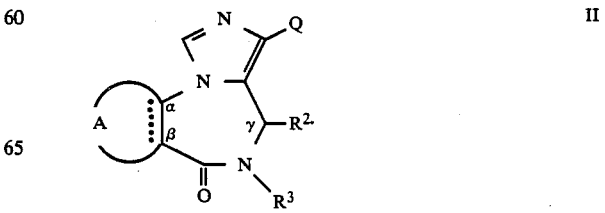

II wherein $R^2$, $R^3$, A have the significance given above and Q has the significance given below, by (a) reacting a compound of formula II, wherein Q signifies the group —$COR^6$ (a) and $R^6$ signifies hydrogen or lower alkyl, with a compound of the general formula $H_2NOR^7$ (III), wherein $R^7$ signifies lower alkyl, or (b) reacting a compound of formula II, wherein Q signifies the group —$C(R^6)$=NOH (b) and $R^6$ signifies hydrogen or lower alkyl, in the presence of a base with a compound of the general formula $X'$—$R^7$ (IV), wherein $R^7$ signifies lower alkyl and $X'$ signifies a leaving group, or (c) cyclizing a compound of formula II, wherein Q signifies the group

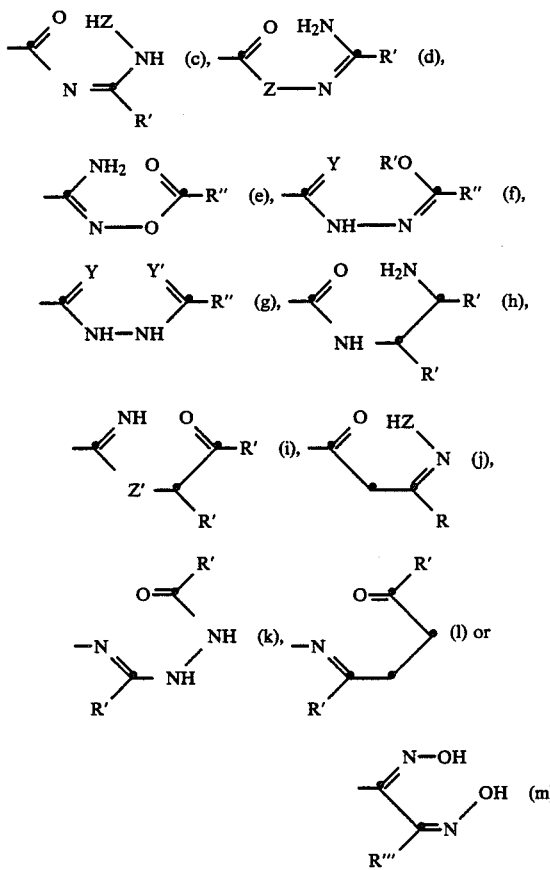

Y and Y' each signify an oxygen or sulphur atom, Z signifies an oxygen atom or the group —$NR^8$—, $R^8$ signifies hydrogen or lower alkyl, Z' signifies a sulphur atom or the group —NH—, R signifies hydrogen, lower alkyl, ($C_3$-$C_6$)-cycloalkyl, lower alkoxy-lower alkyl or hydroxy, R' signifies hydrogen, lower alkyl, ($C_3$-$C_6$)-cycloalkyl, lower alkoxy-lower alkyl or phenyl, R" signifies hydrogen, lower alkyl, ($C_3$-$C_6$)-cycloalkyl, lower alkoxy-lower alkyl, trifluoromethyl or phenyl and R''' signifies hydrogen, lower alkyl, ($C_3$-$C_6$)-cycloalkyl or lower alkoxy-lower alkyl, and, if necessary, dehydrogenating the compound obtained, or (d) cyclizing a compound of formula II, wherein Q signifies the group —CONHNH—COR" (g') and R" has the above significance, in the presence of phosphorus pentasulphide, ammonia or a lower, primary alkylamine, or (e) reacting a compound of formula II, wherein Q signifies the group —C≡N→O (n), with a lower alkyl nitrile which is optionally substituted by lower alkoxy, a ($C_3$-$C_6$)-cycloalkyl nitrile or with ethylene or acetylene which is optionally mono- or disubstituted by lower alkyl, lower alkoxy-lower alkyl or ($C_3$-$C_6$)-cycloalkyl, or reacting a compound of formula II, wherein Q signifies the group —CN (o), with a lower alkyl nitrile oxide which is optionally substituted by lower alkoxy or a ($C_3$-$C_6$)-cycloalkyl nitrile oxide and, if necessary, dehydrogenating the compound obtained, or (f) reacting a compound of formula II, wherein Q signifies the group —CH=O (p), —CH=$NR^{81}$ (q) or —N=$CHR^{IV}$ (r), $R^{81}$ signifies lower alkyl and $R^{IV}$ signifies lower alkyl, ($C_3$-$C_6$)-cycloalkyl or lower alkoxy-lower alkyl, in the presence of a base with p-toluenesulphonylmethyl isocyanide, or (g) cyclizing a compound of formula II, wherein Q signifies the group

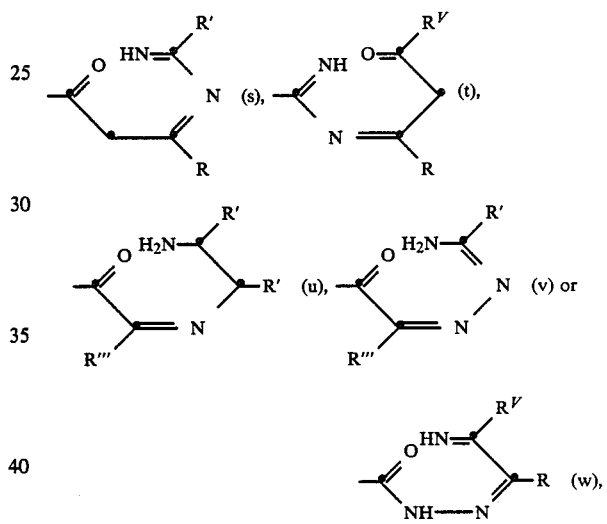

R, R' and R''' have the above significance and $R^V$ signifies hydrogen, lower alkyl, ($C_3$-$C_6$)-cycloalkyl, lower alkoxy-lower alkyl or lower alkoxy, and, if necessary, dehydrogenating the compound obtained, or (h) reacting a compound of formula II, wherein Q signifies the group —CO—NH—$CH_2$—C≡C—$R^{VI}$ (x) and $R^{VI}$ signifies hydrogen, ($C_1$-$C_6$)-alkyl or lower alkoxy-($C_1$-$C_6$)-alkyl, with mercury (II) acetate; or by (i) reacting a compound of the general formula

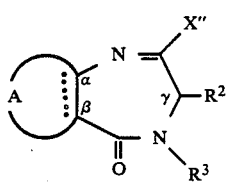

wherein X" signifies a leaving group and $R^2$, $R^3$ and A have the above significance, in the presence of a base with an isonitrile of the general formula

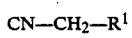

CN—$CH_2$—$R^1$    XX wherein $R^1$ has the above significance; and whereafter (j) if desired, a compound of formula I obtained is converted into a pharmaceutically acceptable acid addition salt.

In a particular embodiment compounds of formula I, wherein $R^1$ signifies 1,2,4-oxadiazol-5-yl which is substituted in the 3-position by $(C_1-C_3)$-alkyl or 1,2,4-oxadiazol-3-yl which is substituted in the 5-position by $(C_1-C_3)$-alkyl, A signifies the group (1), $R^2$ signifies hydrogen, $R^3$ signifies hydrogen or methyl, one of $R^4$ and $R^5$ signifies hydrogen and the other signifies hydrogen, chlorine, fluorine or nitro, are manufactured in accordance with process variant (e) or (i).

In accordance with process variant (a) a compound of formula I, wherein $R^1$ signifies the group (B), can be manufactured by reacting a compound of formula II, wherein Q signifies the group (a), with an O-alkyl-hydroxylamine of formula III. This reaction can be carried out according to methods which are known per se and which are familiar to any person skilled in the art. For example, the corresponding compound of formula II can be reacted with an O-alkyl-hydroxylamine hydrochloride in the presence of water and an acid-binding agent (e.g. sodium carbonate), whereby the reaction can be carried out in a temperature range of about room temperature up to about 50° C.

In accordance with process variant (b) a compound of formula I, wherein $R^1$ signifies the group (B), can be manufactured by alkylating a compound of formula II, wherein Q signifies the group (b), with a compound of formula IV. The leaving group denoted by $X'$ is preferably a halogen atom, e.g. a chlorine or bromine atom, or an alkylsulphonyloxy or arylsulphonyloxy group, e.g. a methanesulphonyloxy or a p-toluenesulphonyloxy group. This reaction is also known per se and familiar to any person skilled in the art.

The cyclization in accordance with process variant (c) can also be carried out according to methods known per se. The choice of the suitable method depends on the nature of the compound to be cyclized. For example, one method comprises heating a corresponding compound of formula II to temperatures up to about 150° C., whereby in this case the presence of a solvent is not absolutely necessary. Other compounds of formula II referred to here can be cyclized by the use of acid in a solvent or solvent mixture at temperatures of about room temperature up to about 150° C. An especially preferred acid is acetic acid, which can simultaneously also serve as the solvent. Depending on the compound of formula II used the cyclization can, however, also be carried out by means of a strong base such as e.g. 1,8-diazabicyclo[5.4.0]undec-7-ene in an inert organic solvent at an elevated temperature. Suitable solvents are, for example, N,N-dimethylformamide and lower alcohols such as n-butanol. In this case the cyclization is preferably carried out at the boiling temperature of the reaction mixture. Certain of the compounds of formula II referred to here cyclize spontaneously and can not be used in isolated form. In other cases it has been found to be convenient to cyclize the compounds of formula II, although they can be isolated, directly or to leave the compounds of formula II to cyclize without isolation from the reaction mixture in which they have been prepared.

Depending on the compound of formula II used there is obtained a cyclization product with a partially unsaturated heterocycle which must subsequently be dehydrogenated. Ususal dehydrogenation agents come into consideration for this purpose. As examples there can be named manganese dioxide in acetone or pyridine (temperature: 20°-80° C.), nickel peroxide in boiling cyclohexane and sulphur in boiling xylene.

The cyclization of a compound of formula II, wherein Q signifies the group (g'), in accordance with process variant (d) is also carried out according to methods which are know per se and which are familiar to any person skilled in the art. When phosphorus pentasulphide is used the cyclization is conveniently carried out in an inert organic solvent such as pyridine or collidine and at a temperature of about 80° C. When ammonia or lower alkyl-amines are used the cyclization is preferably carried out in a lower alcohol such as ethanol and at a temperature up to 120° C., in which case a pressure vessel must be used if necessary.

The reaction of a compound of formula II, wherein Q signifies the group (n), with a lower alkyl nitrile, which is optionally substituted by lower alkoxy, a $(C_3-C_6)$-cycloalkyl nitrile or with ethylene or acetylene which is optionally mono- or disubstituted by lower alkyl, lower alkoxy-lower alkyl or $(C_3-C_6)$-cycloalkyl or of a compound of formula II, wherein Q signifies the group (o), with a lower alkyl nitrile oxide which is optionally substituted by lower alkoxy or a $(C_3-C_6)$-cycloalkyl nitrile oxide in accordance with process variant (e) is a cycloaddition which is known per se. Suitable solvents for this process aspect are, for example, diethyl ether and toluene. The reaction temperature conveniently lies in a range of 20° C. to 80° C. In the case of the reaction of a compound of formula II, wherein Q signifies the group (n), with ethylene which is optionally mono- or disubstituted by lower alkyl, $(C_3-C_6)$-cycloalkyl or lower alkoxy-lower alkyl there is obtained a compound with a partially unsaturated heterocycle which must subsequently be dehydrogenated. Suitable dehydrogenation agents are, for example, manganese dioxide in acetone or pyridine (temperature: 20°-80° C.), nickel peroxide in boiling cyclohexane and sulphur in boiling xylene.

The reaction of a compound of formula II, wherein Q signifies the group (p), (q) or (r), with p-toluenesulphonylmethyl isocyanide in the presence of a base is also carried out according to methods which are known per se. In a preferred embodiment the reaction is carried out by means of an inorganic base such as e.g. potassium carbonate in a boiling, lower alcohol such as e.g. methanol.

Finally, the cyclization of a compound of formula II, wherein Q signifies one of the groups (s) to (w), is also carried out according to methods which are known per se and which are familiar to any person skilled in the art. For example, sulphuric acid, polyphosphoric acid, anhydrous hydrofluoric acid or phosphorus oxychloride can be used as the cyclization agent for the present purpose. Depending on the compound of formula II used there is obtained a cyclization product with a partially unsaturated heterocycle which must subsequently be dehydrogenated. The dehydrogenation agents which are usual for this purpose come into consideration. As examples there can be named manganese dioxide in acetone or pyridine (temperature: 20°-80° C.), nickel peroxide in boiling cyclohexane and sulphur in boiling xylene.

The reaction of a compound of formula II, wherein Q signifies the group (x), with mercury (II) acetate is conveniently carried out in glacial acetic acid at reflux temperature. There are obtained compounds of formula I, wherein $R^1$ signifies an oxazol-2-yl residue which is substituted in the 5-position by the group —CH₂—R^VI in which R^VI has the above significance.

The manufacture of compounds of formula I in accordance with process variant (i) is also carried out according to methods which are known per se. The leaving group denoted by X″ in formula V is preferably a readily cleavable phosphinyl group, for example a group of the formula (R¹⁰O)₂POO—, wherein R¹⁰ signifies lower alkyl or phenyl. As bases there are suitable e.g. alkali metal alkoxides such as potassium tert.-butoxide and alkali metal hydrides such as sodium hydride. Suitable sovents are, for example, dimethylformamide, dimethyl sulphoxide, tetrahydrofuran and the like. The reaction temperature conveniently lies between about −40° C. and about room temperature.

In accordance with process variant (j) a compound of formula I can be converted into a pharmaceutically acceptable acid addition salt. The manufacture of such pharmaceutically acceptable acid addition salts is carried out according to generally usual methods. There come into consideration not only salts with inorganic acids, but also salts with organic acids, for example hydrochlorides, hydrobromides, sulphates, methanesulphonates, p-toluenesulphonates, oxalates, maleates and the like.

The compounds of formula II, wherein Q signifies one of the groups (c)—(n) and (q)—(x), are novel and can be prepared as follows according to methods which are known per se:

A compound of formula II, wherein Q signifies the group (c), can be prepared, for example, by reacting a compound of formula IIa, wherein Q¹ signifies the group —CONH₂, with a compound of the general formula

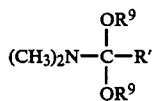    VI wherein R⁹ signifies lower alkyl and R′ has the above significance, and treating the product obtained, a compound of formula II, wherein Q signifies the group —CON=C(R′)—N(CH₃)₂, with hydroxylamine, hydrazine or a lower alkylhydrazine.

A compound of formula II, wherein Q signifies the group (d), can be prepared, for example, by reacting a compound of formula IIa, wherein Q¹ signifies the group —COX and X signifies a leaving group, for example a halogen atom or a 1-imidazolyl group, with a compound of the general formula

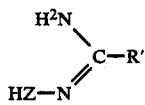    VII wherein Z and R′ have the above significance.

A compound of formula II, wherein Q signifies the group (e), can be prepared, for example, by treating a compound of formula IIa, wherein Q′ signifies the group —CN, with hydroxylamine and reacting the thus-obtained compound of formula II, wherein Q signifies the group —C(NH₂)=NOH, with a reactive derivative of a carboxylic acid of the general formula

 R″—COOH    VIIIa wherein R″ has the above significance, for example with a corresponding anhydride or acid chloride.

A compound of formula II, wherein Q signifies the group (f), can be prepared, for example, by treating a compound of formula IIa, wherein Q¹ signifies the group —COX above, with hydrazine and reacting the resulting compound of formula II, wherein Q signifies the group —CONH—NH₂, with a tri(lower alkyl) orthoester of a carboxylic acid of formula VIIIa above.

A compound of formula II, wherein Q signifies the group (g), can be prepared, for example, by reacting a compound of formula II, wherein Q signifies the group —CONH—NH₂ above with a sulphurizing agent such as phosphorus pentasulphide or 2,4-bis(p-methoxyphenyl)-1,3,2,4-dithiadiphosphetane-2,4-disulphide and/or with a reactive derivative of a carboxylic acid of the general formula

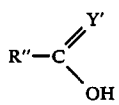    VIII wherein R″ and Y′ have the above significance, or by reacting a compound of formula IIa, wherein Q¹ signifies the group —COX above, with a compound of the general formula

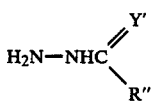    IX wherein R″ and Y′ have the above significance, and, if desired, treating the resulting compound of formula II, wherein Q signifies the group —CONHNHC(R″)=Y′ and R″ and Y′ have the above significance, with a sulphurizing agent such as phosphorus pentasulphide or 2,4-bis(p-methoxyphenyl)-1,3,2,4 -dithiadiphosphetane-2,4-disulphide.

A compound of formula II, wherein Q signifies the group (h), can be prepared by reacting a compound of formula IIa, wherein Q¹ signifies the group —COX above, with a 1,2-diamine of the general formula

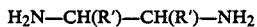 H₂N—CH(R′)—CH(R′)—NH₂    X wherein R′ has the above significance.

A compound of formula II, wherein Q signifies the group (i), can be prepared by converting a compound of formula IIa, wherein Q¹ signifies the group —CN above, with thioacetamide into a compound of formula II, wherein Q signifies the group —C(NH₂)=S, or converting a compound of formula II, wherein Q signifies the above group —C(NH₂)=NOH above, by means of catalytic reduction on Raney-nickel into a compound of formula II, wherein Q signifies the group —C(NH₂)=NH, and reacting the resulting compound with an α-halocarbonyl compound of the general formula

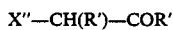 X″—CH(R′)—COR′    XI wherein X″ signifies a halogen atom and R′ has the above significance.

A compound of formula II, wherein Q signifies the group (j), can be prepared by reacting a compound of formula IIa, wherein $Q^1$ signifies the group —COX above, with the anion of a compound of the general formula $$R^9OOC-CH_2COR^V \qquad XII$$

wherein $R^V$ and $R^9$ have the above significance, and reacting the compound of formula II, wherein Q signifies the group —CO—CH$_2$—COR$^V$ and $R^V$ has the above significance, which is obtained after hydrolysis of the group —COOR$^9$ and decarboxylation, with hydroxylamine, hydrazine or a lower alkylhydrazine.

A compound of formula II, wherein Q signifies the group (k) or (l), can be prepared by reacting a compound of formula IIa, wherein $Q^1$ signifies the group —NH$_2$, with a compound of the general formula $$R'-CO-NHNH-COR' \qquad XIV,$$

or $$R'-CO-CH_2CH_2-COR' \qquad XV$$

wherein R' has the above significance.

A compound of formula II, wherein Q signifies the group (m), can be prepared by oxidizing a compound of formula II, wherein Q signifies the group —COCH$_2$R''' and R''' has the above significance, in the α-position to the carbonyl group with an oxidation agent such as manganese dioxide and reacting the resulting compound of formula II, wherein Q signifies the group —COCO—R''' and R''' has the above significance, with hydroxylamine.

A compound of formula II, wherein Q signifies the group (n), can be prepared by halogenating the oxime group in a compound of formula IIa, wherein $Q^1$ signifies the group —CH=NOH, and then dehydrohalogenating.

A compound of formula II, wherein Q signifies the group (q) or (r), can be prepared by reacting a compound of formula IIa, wherein $Q^1$ signifies the group —CH=O or —NH$_2$, with an amine of the general formula $$H_2N-R^{81} \qquad XVI$$

wherein $R^{81}$ has the above significance, or with an aldehyde of the general formula $$O=CH-R^{IV} \qquad XVII$$

wherein $R^{IV}$ has the above significance.

A compound of formula II, wherein Q signifies the group (s), can be prepared by reacting a compound of formula II, wherein X signifies the group —CO—CH$_2$—COR$^V$ above, with an amidine of the general formula

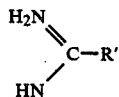 XVIII wherein R' has the above significance.

A compound of formula II, wherein Q signifies the group (t), can be prepared by reacting a compound of formula II, wherein Q signifies the group —C(NH$_2$)=NH above, with a compound of formula XIII above.

A compound of formula II, wherein Q signifies the group (u) or (v), can be prepared by reacting a compound of formula II, wherein Q signifies the group —COCO—R''' above, with a compound of formula X above or with a compound of formulae VII above, wherein Z signifies the group —NH—.

A compound of formula II, wherein Q signifies the group (w), can be prepared by reacting a compound of formula II, wherein Q signifies the group —CONH—NH$_2$ above, with a compound of the general formula $$R^V-CO-CO-R^V \qquad XIX$$

wherein $R^V$ has the above significance, and reacting the resulting compound of formula II, wherein Q signifies the group —CONH—N=C(R)—COR$^V$ and R and $R^V$ have the above significance, with ammonia or a derivative thereof (e.g. ammonium acetate).

A compound of formula II, wherein Q signifies the group (x), can be prepared by reacting a compound of formula IIa, wherein $Q^1$ signifies the group —COX above, with a compound of the formula H$_2$N—CH$_2$—C≡C—R$^{VI}$, wherein R$^{VI}$ has the above significance.

As already mentioned above, it is not necessary (and in certain cases also not possible) to isolate the compounds of formula II, wherein Q signifies one of the groups (c)-(m) or (s)-(w); it has frequently been found to be convenient to cyclize these compounds directly or to leave these compounds to cyclize without isolation from the reaction mixture in which they have been prepared.

The compounds of formula II, wherein Q signifies one of the above groups (c)-(n) or (q)-(x) or the group —CON=C(R')—N(CH$_3$)$_2$—C(NH$_2$)=NOH, —C(=Y)—NH—NH$_2$, —C(=Y)—NHNHC(R'')=Y', —C(NH$_2$)=Z', —CO—CH$_2$—COR$^V$, —COCO—R''' or —CONH—N=C(R)—COR$^V$, are novel and are likewise an object of the present invention. Many of the Examples following hereinafter contain detailed information concerning the preparation of these novel compounds of formula II.

As already mentioned, the compounds of formula IIa are known per se. The compounds of formula IIa which have not been described previously can be prepared in analogy to the known representatives of this class of substance. Many of the Examples following hereinafter also contain detailed information concerning the preparation of compounds of formula IIa.

The compounds of formulae V and XX used as starting materials are known or can be prepared in analogy to the known representatives of these classes of substances.

As mentioned earlier, the compounds of formula I are novel; they possess extremely valuable pharmacodyamic properties and have only a low toxicity. They possess as a common characteristic a pronounced affinity to the central benzodiazepine receptors and have pronounced anxiolytic, anticonvulsant, muscle relaxant and sedative-hypnotic properties.

The affinity of compounds of general formula I to the central benzodiazepine receptors was determined according to the method described in Life Science 20, 2101–2110 (1977) and Science 198, 849–851 (1077). According to this method, the inhibition of the binding of tritiated diazepam at the specific benzodiazepine receptors in the cerebral cortex by the respective test substances is ascertained. The IC$_{50}$ ("50% inhibiting concentration") is that concentration of the respective test substance which brings about a 50 percent inhibition of the specific binding of the tritiated diazepam at the specific benzodiazepine receptors in the cerebral cortex.

The central properties of the compounds of formula I in accordance with the invention can be determined, for example, in the antipentetrazole test which is described hereinafter and which is generally recognized for recording anticonvulsant properties.

In this animal experiment the compound under investigation is administered orally to female rats weighing 60–80 g and 30 minutes later there are administered i.p. 120 mg/kg of pentetrazole, which causes emprosthotonus and tonic stretchings of the fore and/or hind limbs in unprotected experimental animals 1–4 minutes after the injection. Ten experimental animals are used per dosage of test substance. After counting the protected experimental animals the ED$_{50}$ is determined according to the Probit method. The ED$_{50}$ is that dosage which protects 50% of the experimental animals from the spasmodic seizures caused by pentetrazole.

The results which have been obtained with representative members of the class of compound defined by general formula I in the experiments described previously are compiled in the following Table. Moreover, the Table contains data concerning the acute toxicity of some of these compounds (LD$_{50}$ in mg/kg in the case of single oral administration to mice).

| Compounds of formula I, wherein R$^1$ | R$^2$ | R$^3$ | R$^4$ | R$^5$ | Configuration | IC$_{50}$ in nM/l | Antipentetrazole test, ED$_{50}$ in mg/kg p.o. | Toxicity LD$_{50}$ in mg/kg p.o. |
|---|---|---|---|---|---|---|---|---|
| 3-methyl-1,2,4-oxadiazol-5-yl (O—N, N, CH$_3$) | | —CH$_2$CH$_2$CH$_2$— | Cl | H | (S) | 2.3 | 0.08 | 2000–4000 |
| 3-methyl-1,2,4-oxadiazol-5-yl (N—N, O, CH$_3$) | | —CH$_2$CH$_2$CH$_2$— | Cl | H | (S) | 8.4 | 2.7 | 312–625 |
| 3-methyl-1,2,4-oxadiazol-5-yl (O—N, N, CH$_3$) | H | —CH$_3$ | Cl | H | — | 3.9 | 0.43 | 1250–2500 |
| 3-methyl-1,2,4-oxadiazol-5-yl (O—N, N, CH$_3$) | | —CH$_2$CH$_2$CH$_2$— | Br | H | (S) | 2.1 | 0.068 | 2500–5000 |
| 3-methyl-1,2,4-oxadiazol-5-yl (O—N, N, CH$_3$) | | —CH$_2$CH$_2$CH$_2$— | Cl | F | (S) | 5.2 | 0.082 | 1250–2500 |
| (N—O, N, CF$_3$) | | —CH$_2$CH$_2$CH$_2$— | Cl | H | (S) | 9.6 | 1.2 | — |
| (O—N, N, CH$_3$) | | —CH$_2$—CH$_2$— | CF$_3$ | H | (S) | 3.7 | 0.021 | — |
| —CH=NOCH$_3$ | | —CH$_2$CH$_2$— | Cl | H | (S) | 10 | 0.63 | — |

-continued

| Compounds of formula I, wherein R¹ | R² | R³ | R⁴ | R⁵ | Configuration | $IC_{50}$ in nM/l | Antipentetrazole test, $ED_{50}$ in mg/kg p.o. | Toxicity $LD_{50}$ in mg/kg p.o. |
|---|---|---|---|---|---|---|---|---|
| [isoxazoline with N-CH₃, =N-] | —CH₂CH₂— | | Cl | H | (R,S) | 10 | 0.32 | — |
| [isoxazoline with N-cyclopropyl, =N-] | H | CH₃ | Cl | H | — | 4.5 | 0.034 | — |
| [isoxazoline with N-cyclopropyl, =N-] | —CH₂CH₂CH₂— | | Cl | H | (S) | 2.2 | 0.20 | 1250–2500 |
| [isoxazoline with N-cyclopropyl, =N-] | H | —CH₃ | H | F | — | 5.6 | 0.23 | — |
| [isoxazoline with N-CH₂OCH₃, =N-] | —CH₂CH₂CH₂ | | Cl | H | (S) | 5.2 | 0.39 | — |

The compounds of formula I and their pharmaceutically acceptable acid addition salts can be used as medicaments, e.g. in the form of pharmaceutical preparations. The pharmaceutical preparations can be administered orally, e.g. in the form of tablets, coated tablets, dragees, hard and soft gelatine capsules, solutions, emulsions or suspensions. The administration can, however, also be carried out rectally, e.g. in the form of suppositories, or parenterally, e.g. in the form of injection solutions.

For the manufacture of pharmaceutical preparations the products in accordance with the invention can be processed with pharmaceutically inert, inorganic or organic carriers. As such carriers there can be used for tablets, coated tablets, dragees and hard gelatine capsules, for example, lactose, maize starch or derivatives thereof, talc, stearic acid or its salts and the like. Suitable carriers for soft gelatine capsules are, for example, vegetable oils, waxes, fats, semi-solid and liquid polyols and the like; depending on the nature of the active substance no carriers may, however, be required in the case of soft gelatine capsules. Suitable carriers for the manufacture of solutions and syrups are, for example, water, polyols, saccharose, invert sugar, glucose and the like. Suitable carriers for injection solutions are, for example, water, alcohols, polyols, glycerine, vegetable oils and the like. Suitable carriers for suppositories are, for example, natural or hardened oils, waxes, fats, semi-liquid or liquid polyols and the like.

The pharmaceutical preparations can also contain preserving agents, solubilizing agents, stabilizing agents, wetting agents, emulsifying agents, sweetening agents, colouring agents, flavouring agents, salts for varying the osmotic pressure, buffers, coating agents or antioxidants. They can also contain still other therepeutically valuable substances.

As mentioned earlier, medicaments containing a compound of formula I or a pharmaceutically acceptable acid addition salt thereof are also an object of the present invention, as is a process for the manufacture of such medicaments, which process comprises bringing one or more compounds of formula I or pharmaceutically acceptable acid addition salts thereof and, if desired, one or more therepeutically valuable substances into a galenical administration form.

As mentioned earlier, the compounds of formula I and their pharmaceutically acceptable acid addition salts can be used in the control or prevention of illnesses and especially in the control of convulsions and anxiety states. The dosage can vary within wide limits and is, of course, fitted to the individual requirements in each particular case. In general, in the case of oral administration a daily dosage of about 0.01 mg to 100 mg comes into consideration.

The following Examples are intended to illustrate the present invention in more detail, but are not intended to limit its extent in any manner. All temperatures are given in degrees Celsius.

EXAMPLE 1

(a) 14.5 g (47.7 mmol) of (S)-8-chloro-12,12a-dihydro-9-oxo-9H,11H-azeto[2,1-c]imidazo[1,5-a][1,4]benzodiazepine-1-carboxylic acid are suspended in 55 ml of N,N-dimethylformamide, whereupon the suspension is treated portionwise with 10.3 g (63.5 mmol) of 1,1'-carbonyldiimidazole and the mixture is stirred at room temperature for 1 hour and at 50° for 1.5 hours. The mixture is then poured into 250 ml of water and extracted four times with methylene chloride. The combined organic extracts are washed three times with water, dried over magnesium sulphate and evaporated. For purification, the residue is crystallized by means of ethyl acetate. There is obtained 1-[[(S)-8-chloro-12,12a-dihydro-9-oxo-9H,11H-azeto[2,1-c]imidazo[1,5-a][1,4]benzodiazepin-1-yl]carbonyl]imidazole of decomposition point 223°–225°.

(b) A suspension of 14.86 g (42 mmol) of 1-[[(S)-8-chloro-12,12a-dihydro-9-oxo-9H,11H-azeto[2,1-c]imidazo[1,5-a][1,4-benzodiazepin-1-yl]carbonyl]-imidazole in 40 ml of N,N-dimethylformamide is treated with 7.3 ml (about 96 mmol) of a 25 percent aqueous ammonia solution and the mixture is stirred at room temperature for 30 minutes. The mixture is then poured into 220 ml of water, the product is filtered off after 1 hour, rinsed with water and dried at 80° in vacuo. There is obtained (S)-8-chloro-12,12a-dihydro-9-oxo-9H,11H-azeto[2,1-c]imidazo[1,5-a][1,4]benzodiazepine-1-carboxamide with a melting point >300°.

(c) A mixture of 10 g (33 mmol) of (S)-8-chloro-12,12a-dihydro-9-oxo-9H,11H-azeto[2,1-c]imidazo[1,5-a][1,4]benzodiazepine-1-carboxamide and 35 ml of N,N-dimethylformamide is treated with 21 ml (135.5 mmol) of N,N-dimethylacetamide dimethyl acetal and the mixture is stirred at 115° for 2 hours. The brown solution is then evaporated to dryness.

(d) The residue (containing the (R,S) compound of formula II, wherein Q signifies the group —CON=C(CH$_3$)N(CH$_3$)$_2$, R$^2$ and R$^3$ together signify dimethylene, R$^4$ signifies chlorine and R$^5$ signifies hydrogen) is dissolved in a mixture of 12 ml of water, 12 ml of 4N sodium hydroxide and 46 ml of dioxan, 3.2 g (46 mmol) of hydroxylamine hydrochloride and 64 ml of glacial acetic acid are added thereto and the mixture is stirred at 90° for 1 hour. The reaction mixture is then diluted with 170 ml of water, extracted four times with methylene chloride, the organic extracts are dried over magnesium sulphate and evaporated. The crude product is chromatographed on silica gel while eluting with methylene chloride/acetone (9:1) and subsequently recrystallized three times from N,N-dimethylformamide. There is obtained (R,S)-8-chloro-12,12a-dihydro-1-(3-methyl-1,2,4-oxadiazol-5-yl)-9H,11H-azeto[2,1-c]imidazo[1,5-a][1,4-benzodiazepin-9-one of melting point 236°–237°.

EXAMPLE 2

(a) A mixture of 40 g (131.9 mmol) of ethyl 8-fluoro-5,6-dihydro-5-methyl-6-oxo-4H-imidazo[1,5-a][1,4-benzodiazepine-3-carboxylate, 5.9 g (147.5 mmol) of sodium hydroxide, 250 ml of ethanol and 200 ml of water is heated to boiling under reflux for 15 minutes. The mixture is then neutralized by the addition of 36.8 ml (147.5 mmol) of 4N hydrochloric acid, the ethanol is distilled off in vacuo, the residue is diluted with about 200 ml of water and cooled to about 5°. The product is filtered off under suction, rinsed with water and dried at 80°–90° in a high vacuum. There is obtained 8-fluoro-5,6-dihydro-5-methyl-6-oxo-4H-imidazo[1,5a][1,4]benzodiazepine-3-carboxylic acid of decomposition point 280°.

(b) 13.76 g (50 mmol) of 8-fluoro-5,6-dihydro-5-methyl-6-oxo-4H-imidazo[1,5-a][1,4-benzodiazepine-3-carboxylic acid are suspended in 100 ml of N,N-dimethylformamide, whereupon the suspension is treated portionwise with 20.6 g (123 mmol) of 1,1'-carbonyldiimidazole and the mixture is stirred at room temperature for 20 minutes and at 70°–80° for 6 hours. The mixture is then poured into 250 ml of water, the product is filtered off under suction after 1 hour, rinsed with water and dried at 85° in a high vacuum. There is obtained 1-[[8-fluoro-5,6-dihydro-5-methyl-6-oxo-4H-imidazo[1,5-a][1,4]-benzodiazepin-3-yl]carbonyl]-imidazole of decomposition point 295°–296°.

(c) 15 g (46.1 mmol) of 1-[[8-fluoro-5,6-dihydro-5-methyl-6-oxo-4H-imidazo[1,5-a][1,4]benzodiazepin-3-yl]carbonyl]imidazole are suspended in 75 ml of N,N-dimethylformamide, whereupon the suspension is treated with 7.8 ml (102 mmol) of a 25 percent aqueous ammonia solution, the mixture is stirred at room temperature for 0.75 hour and then poured into 300 ml of water. The product is filtered off under suction after 1 hour, rinsed with water and dried at 85° in a vacuum drying oven. There is obtained 8-fluoro-5,6-dihydro-5-methyl-6-oxo-4H-imidazo[1,5-a][1,4]benzodiazepine-3-carboxamide of melting point 272°–273°.

(d) 5.48 g (20 mmol) of 8-fluoro-5,6-dihydro-5-methyl-6-oxo-4H-imidazo[1,5-a][1,4]-benzodiazepine-3-carboxamide are suspended in 15 ml of N,N-dimethylformamide, whereupon the suspension is treated with 5.6 ml (36 mmol) of N,N-dimethylacetamide dimethyl acetal, the mixture is stirred at 115° for 1 hour and 5 ml of toluene and 40 ml of diethyl ether are added to the solution obtained. The mixture is then cooled to about 5°, the product is filtered off under suction, rinsed with diethyl ether and dried at 80° in vacuo.

(e) The thus-obtained intermediate (namely the compound of formula II, wherein Q signifies the group —CON=C(CH$_3$)N(CH$_3$)$_2$, R$^2$ signifies hydrogen, R$^3$ signifies methyl, R$^4$ signifies hydrogen and R$^5$ signifies fluorine) is treated successively with 6.6 ml of water, 6.6 ml of 4N sodium hydroxide, 25 ml of dioxan, 1.81 g (26 mmol) of hydroxylamine hydrochloride and 35 ml of glacial acetic acid, whereupon the mixture is stirred at 90° for 20 minutes. After the addition of 120 ml of water the mixture is cooled to about 0°, the product is filtered off under suction, rinsed with water and dried at 80° in vacuo. The crude product is chromatographed on silica gel while eluting with ethyl acetate and subsequently recrystallized from methylene chloride/ethyl acetate. There is obtained 8-fluoro-5,6-dihydro-5-methyl-3-(3-methyl-1,2,4-oxadiazol-5-yl)-4H-imidazo[1,5-a][1,4]benzodiazepin-6-one of melting point 244°–245°.

EXAMPLE 3

(a) A mixture of 37.3 g (116.6 mmol) of ethyl 7-chloro-5,6-dihydro-5-methyl-6-oxo-4H-imidazo[1,5-a][1,4]benzodiazepine-3-carboxylate, 5.276 g (131.9 mmol) of sodium hydroxide, 150 ml of ethanol and 100 ml of water is heated to boiling under reflux for 15 minutes. The mixture is then neutralized by the addition of 132 ml of 1N hydrochloric acid, the ethanol is distilled off in vacuo and the residue is diluted with 100 ml of water. The mixture is cooled to about 0°, the product is filtered off under suction, rinsed with water and dried at 80° in a high vacuum. There is obtained 7-chloro-5,6-dihydro-5-methyl-6-oxo-4H-imidazo[1,5-a][1,4]benzodiazepine-3-carboxylic acid of decomposition point 283°–284°.

(b) 7.3 g (25 mmol) of 7-chloro-5,6-dihydro-5-methyl-6-oxo-4H-imidazo[1,5-a][1,4]benzodiazepine-3-carboxylic acid are suspended in 50 ml of N,N-dimethylformamide, whereupon the suspension is treated with 5.67 g (34 mmol) of 1,1'-carbonyldiimazole and the mixture is stirred at room temperature for a further 0.75 hour and subsequently at 60° for 2 hours. The mixture is then poured into 100 ml of water, the product is filtered off under suction after 1 hour, rinsed with water and dried at 80° in a high vacuum. There is obtained 1-[[7-chloro-5,6-dihydro-5-methyl-6-oxo-4H-imidazo[1,5-a][1,4]benzodiazepin-3-yl]carbonyl]imidazole of decomposition point 242°–244°.

(c) 7 g (20.5 mmol) of 1-[[7-chloro-5,6-dihydro-5-methyl-6-oxo-4H-imidazo[1,5-a][1,4]benzodiazepin-3-yl]carbonyl]imidazole are suspended in 20 ml of N,N-dimethylformamide, whereupon the suspension is treated with 3.5 ml (about 46 mmol) of a 25 percent aqueous ammonia solution, the mixture is stirred at room temperature for 1 hour and then poured into 10 ml of water. The product is filtered off under suction after 1 hour, rinsed with water and dried at 80° in a high vacuum. There is obtained 7-chloro-5,6-dihydro-5-methyl-6-oxo-4H-imidazo[1,5-a][1,4]benzodiazepine-3-carboxamide of melting point 266°–268°.

(d) A suspension of 4.5 g (15.5 mmol) of 7-chloro-5,6-dihydro-5-methyl-6-oxo-4H-imidazo[1,5-a][1,4]benzodiazepine-3-carboxamide in 15 ml of N,N-dimethylformamide is treated with 4.8 ml (31 mmol) of N,N-dimethylacetamide dimethyl acetal and the mixture is stirred at 115° for 2 hours. The solution is then diluted with 5 ml of toluene and 40 ml of diethyl ether, cooled to 0°, the product is filtered off under suction, rinsed with diethyl ether and dried at 80° in vacuo.

(e) The thus-obtained intermediate (namely the compound of formula II, wherein Q signifies the group —CON=C(CH$_3$)N(CH$_3$)$_2$, R$^2$ signifies hydrogen, R$^3$ signifies methyl, R$^4$ signifies chlorine and R$^5$ signifies hydrogen) is treated with 5.2 ml of water, 5.2 ml of 4N sodium hydroxide, 20 ml of dioxan, 1.42 g (20.4 mmol) of hydroxylamine hydrochloride and 28 ml of glacial acetic acid, whereupon the mixture is stirred at 90° for 30 minutes. The solution is then diluted with 100 ml of water, cooled to 0°, the product is filtered off under suction, rinsed with water and dried at 85° in vacuo. For purification, the crude product is chromatographed on silica gel while eluting with ethyl acetate and subsequently recrystallized from methylene chloride/ethyl acetate. There is obtained 7-chloro-5,6-dihydro-5-methyl-3-(3-methyl-1,2,4-oxadiazol-5-yl)-4H-imidazo[1,5-a][1,4]benzodiazepin-6-one of melting point 212°–213°.

EXAMPLE 4

(a) A mixture of 4.7 g (12 mmol) of t-butyl (S)-8-chloro-7-fluoro-11,12,13,13a-tetrahydro-9-oxo-9H-imidazo[1,5-a]pyrrolo[2,1-c][1,4]benzodiazepine-1-carboxylate and 24 ml of 1N hydrochloric acid is heated to boiling under reflux for 1.5 hours. The mixture is then cooled to about 5°, the product is filtered off under suction, rinsed with water and dried at 85° in vacuo.

There is obtained (S)-8-chloro-7-fluoro-11,12,13,13a-tetrahydro-9-oxo-9H-imidazo[1,5-a]pyrrolo[2,1-c][1,4]benzodiazepine-1-carboxylic acid of decomposition point 261°–263°.

(b) 3 g (8.9 mmol) of (S)-8-chloro-7-fluoro-11,12,13,13a-tetrahydro-9-oxo-9H-imidazo[1,5-a]pyrrolo[2,1-c][1,4]benzodiazepine-1-carboxylic acid are suspended in 12 ml of N,N-dimethylformamide, whereupon the suspension is treated with 2.02 g (12 mmol) of 1,1'-carbonyldiimazole, the mixture is stirred at room temperature for a further 0.5 hour, then poured into 80 ml of water, the product is filtered off under suction, washed with water and dried at 80°–90° in a high vacuum. There is obtained 1-[[(S)-8-chloro-7-fluoro-11,12,13,13a-tetrahydro-9-oxo-9H-imidazo[1,5-a][1,4]pyrrolo[2,1-c][1,4]benzodiazepin-1-yl]carbonyl]imidazole of decomposition point 273°–274°.

(c) A suspension of 6.93 g (18 mmol) of 1-[[(S)-8-chloro-7-fluoro-11,13,13,13a-tetrahydro-9-oxo-9H-imidazo[1,5-a]pyrrolo[2,1-c][1,4]benzodiazepin-1-yl]carbonyl]imidazole in 20 ml of N,N-dimethylformamide is treated with 3 ml (about 39 mmol) of a 25 percent aqueous ammonia solution and the mixture is stirred at room temperature for 1 hour. The mixture is then poured into 100 ml of water, the product is filtered off under suction after 10 minutes, rinsed with water and dried at 80°–90° in a high vacuum. There is obtained (S)-8-chloro-7-fluoro-11,12,13,13a-tetrahydro-9-oxo-9H-imidazo[1,5-a]pyrrolo[2,1-c][1,4]benzodiazepine-1-carboxamide with a melting point >300°.

(d) A suspension of 5.35 g (16 mmol) of (S)-8-chloro-7-fluoro-11,12,13,13a-tetrahydro-9-oxo-9H-imidazo[1,5-a]pyrrolo[2,1-c][1,4]benzodiazepine-1-carboxamide in 20 ml of N,N-dimethylformamide is treated with 4.5 ml (30.7 mmol) of N,N-dimethylacetamide dimethyl acetal and the mixture is stirred at 115° for 1 hour. The mixture is then cooled to 5°, diluted with 20 ml of diethyl ether, the product is filtered off under suction after 30 minutes, rinsed with diethyl ether and dried at 80° in vacuo.

(e) The thus-obtained intermediate (namely the (S) compound of formula II, wherein Q signifies the group —CON=C(CH$_3$)N(CH$_3$)$_2$, R$^2$ and R$^3$ together signify trimethylene, R$^4$ signifies chlorine and R$^5$ signifies fluorine) is treated with 4.3 ml of water, 4.3 ml of 4N sodium hydroxide, 16 ml of dioxan, 1.16 g (16.7 mmol) of hydroxylamine hydrochloride and 22.5 ml of glacial acetic acid, whereupon the mixture is stirred at 90° for 35 minutes. The solution is subsequently diluted with 120 ml of water, cooled to 0°, the product is filtered off under suction, rinsed with water and dried at 80° in vacuo. For purification, the crude product is chromatographed on silica gel while eluting with methylene chloride/ethyl acetate (1:4). After subsequent recrystallization from methylene chloride/ethyl acetate there is obtained (S)-8-chloro-7-fluoro-11,12,13,13a-tetrahydro-1-(3-methyl-1,2,4-oxadiazol-5-yl)-9H-imidazo[1,5-a]pyrrolo[2,1-c][1,4]benzodiazepin-9-one of melting point 245°–246°.

EXAMPLE 5

(a) A mixture of 10.5 g (25.1 mmol) of t-butyl (S)-8-bromo-11,12,13,13a-tetrahydro-9-oxo-9H-imidazo[1,5-a]pyrrolo[2,1-c][1,4]benzodiazepine-1-carboxylate and 50 ml of 1N hydrochloric acid is heated to boiling under reflux for 1 hour. The mixture is then cooled to 0°, the product is filtered off under suction, rinsed with water and dried at 90° in a high vacuum. There is obtained (S)-8-bromo-11,12,13,13a-tetrahydro-9-oxo-9H-imidazo[1,5-a]pyrrolo[2,1-c][1,4]lbenzodiazepine-1-carboxylic acid of decomposition point 271°.

(b) A mixture of 8.98 g (24.8 mmol) of (S)-8-bromo-11,12,13,13a-tetrahydro-9-oxo-9H-imidazo[1,5-a]pyrrolo[2,1-c][1,4]benzodiazepine-1-carboxylic acid and 5.62 g (33.7 mmol) of 1,1'-carbonyldiimidazole in 40 ml of N,N-dimethylformamide is stirred at room temperature for 25 minutes and at 55° for 1.5 hours. The mixture is then poured into 90 ml of water, the product is filtered off under suction after 30 minutes, rinsed with water and dried at 80°–90° in a high vacuum. There is obtained 1-[[(S)-8-bromo-11,12,13,13a-tetrahydro-9-oxo-9H-imidazo[1,5-a]pyrrolo[2,1-c][1,4]benzodiazepin-1-yl]carbonyl]imidazole of melting point 215°–217°.

(c) A suspension of 8.8 g (21.3 mmol) of 1-[[(S)-8-bromo-11,12,13,13a-tetrahydro-9-oxo-9H-imidazo[1,5-a]pyrrolo[2,1-c][1,4]benzodiazepin-1-yl]carbonyl]imidazole in 20 ml of N,N-dimethylformamide is treated with 3.6 ml (about 47 mmol) of a 25 percent aqueous ammonia solution and the mixture is stirred at room temperature for 1 hour. The mixture is then poured into 100 ml of water, the product is filtered off under suction after 15 minutes, rinsed with water and dried at 80° in a high vacuum. There is obtained (S)-8-bromo-11,12,13,13a-tetrahydro-9-oxo-9H-imidazo[1,5-a]pyrrolo[2,1-c][1,4]benzodiazepine-1-carboxamide of decomposition point 296°.

(d) A suspension of 4.33 g (12 mmol) of (S)-8-bromo-11,12,13,13a-tetrahydro-9-oxo-9H-imidazo[1,5-a]pyrrolo[2,1-c][1,4]benzodiazepine-1-carboxamide in 15 ml of N,N-dimethylformamide is treated with 3.4 ml (23.2 mmol) of N,N-dimethylacetamide dimethyl acetal and the mixture is stirred at 115° for 70 minutes. The suspension is then cooled to 0°, the product is filtered off under suction, rinsed with N,N-dimethylformamide and diethyl ether and dried at 80° in a high vacuum.

(e) The thus-obtained intermediate (namely the (S) compound of formula II, wherein Q signifies the group —CON=C(CH$_3$)N(CH$_3$)$_2$, R$^2$ and R$^3$ together signify trimethylene, R$^4$ signifies bromine and R$^5$ signifies hydrogen) is then treated with 3.5 ml of water, 3.5 ml of 4N sodium hydroxide, 13 ml of dioxan, 0.96 g (13.8 mmol) of hydroxylamine hydrochloride and 18.5 ml of glacial acetic acid, whereupon the mixture is stirred at 90° for 20 minutes. The solution is then diluted with about 80 ml of water, cooled to 0°, the product is filtered off under suction, rinsed with water and dried at 85° in vacuo. For purification, the crude product is chromatographed on silica gel while eluting with methylene chloride/ethyl acetate (1:4). After recrystallization from methylene chloride/ethyl acetate there is obtained (S)-8-bromo-11,12,13,13a-tetrahydro-1-(3-methyl-1,2,4-oxadiazol-5-yl)9H-imidazo[1,5-a]pyrrolo[2,1-c][1,4]benzodiazepin-9-one of melting point 237°–238°.

EXAMPLE 6

(a) 6.33 g (20 mmol) of (S)-8-chloro-11,12,13,13a-tetrahydro-9-oxo-9H-imidazo[1,5-a]pyrrolo[2,1-c][1,4]benzodiazepine-1-carboxamide are suspended in 25 ml of N,N-dimethylformamide, whereupon the suspension is treated with 12.4 ml (85 mmol) of N,N-dimethylacetamide dimethyl acetal and the mixture is stirred at 115° for 2 hours. The suspension is left to cool in a ice-bath for 1 hour, the product is filtered off under suction, rinsed with N,N-dimethylformamide and diethyl ether and dried at 80° in a high vacuum.

(b) The thus-obtained intermediate (namely the (S) compound of formula II, wherein Q signifies the group —CO—N=C(CH$_3$)N(CH$_3$)$_2$, R$^2$ and R$^3$ together signify trimethylene, R$^4$ signifies chlorine and R$^5$ signifies hydrogen) is then treated with 6.2 ml of water, 6.2 ml (24.8 mmol) of 4N sodium hydroxide, 24 ml of dioxan, 1.67 g (24 mmol) of hydroxylamine hydrochloride and 33 ml of glacial acetic acid. The mixture is stirred at 90° for 40 minutes and the solution is then diluted with 85 ml of water. After cooling to 0° the product is filtered off under suction, rinsed with water and dried at 80° in vacuo. The crude product is chromatographed on silica gel, the elution being carried out with methylene chloride/ethyl acetate (3:2) and then with ethyl acetate. After recrystallization from methylene chloride/toluene there is obtained (S)-8-chloro-11,12,13,13a-tetrahydro-1-(3-methyl-1,2,4-oxadiazol-5-yl)-9H-imidazo[1,5-a]pyrrolo[2,1-c][1,4]benzodiazepin-9-one of melting point 233°–234°.

EXAMPLE 7

(a) 368 mg (1 mmol) of 1-[[(S)-8-chloro-11,12,13,13a-tetrahydro-9-oxo-9H-imidazo[1,5-a]pyrrolo[2,1-c][1,4]benzodiazepin-1-yl]carbonyl]imidazole are dissolved in 7 ml of N,N-dimethylformamide, whereupon the solution is treated with 111 mg (1.5 mmol) of acetamidoxime and the mixture is heated to 60° for 20 hours. The reaction mixture is then poured in 30 ml of water, extracted five times with methylene chloride, the combined organic extracts are dried over magnesium sulphate and evaporated to dryness.

(b) The residue (containing the (S) compound of formula II, wherein Q signifies the group —COON=C(CH$_3$)NH$_2$, R$^2$ and R$^3$ together signify trimethylene, R$^4$ signifies chlorine and R$^5$ signifies hydrogen) is dissolved in 5 ml of glacial acetic acid and the solution is stirred at 120° for 2 hours. The reaction mixture is subsequently evaporated and the residue is chromatographed on silica gel while eluting with ethyl acetate. After evaporation of the eluate there is obtained (S)-8-chloro-11,12,13,13a-tetrahydro-1-(3-methyl-1,2,4-oxadiazol-5-yl)-9H-imidazo[1,5-a]pyrrolo[2,1-c][1,4]benzodiazepin-9-one of melting point 230°–231°.

EXAMPLE 8

(a) A mixture of 3.68 g (10.4 mmol) of 1-[[(S)-8-chloro-12,12a-dihydro-9-oxo-9H,11H-azeto[2,1-c]imidazo[1,5-a][1,4]benzodiazepin-1-yl]carbonyl]imidazole, 1 g (13.5 mmol) of acetamidoxime and 20 ml of N,N-dimethylformamide is stirred at 55°–60° for 2.25 hours. The suspension is then poured into 80 ml of water, the product is filtered off under suction and rinsed with water. After drying at 80°–90° in a high vacuum there is obtained 0-[[(S)-8-chloro-12,12a-dihydro-9-oxo-9H,11H-azeto[2,1-c]imidazo[1,5-a][1,4]benzodiazepin-1-yl]carbonyl]acetamidoxime of decomposition point 267°.

(b) 3.35 g (9.3 mmol) of 0-[[(S)-8-chloro-12,12a-dihydro-9-oxo-9H,11H-azeto[2,1-c]imidazo[1,5-a][1,4]benzodiazepine-1-yl]carbonyl]acetamidoxime are treated with 15 ml of glacial acetic acid, whereupon the mixture is stirred at 120° for 1.5 hours. The solution is then evaporated in vacuo and the residue is chromatographed on silica gel while eluting with ethyl acetate. By subsequent recrystallization from methylene chloride/ethyl acetate there is obtained (S)-8-chloro-12,12a-dihydro-1-(3-methyl-1,2,4-oxadiazol-5-yl)-9H,11H- azeto[2,1-c]imidazo[1,5-a][1,4]benzodiazepin-9-one of melting point 239°–240°.

EXAMPLE 9

(a) A solution of 7.1 g (26.3 mmol) of (S)-1,10a-dihydro-5-(trifluoromethyl)azeto[2,1-c][1,4]benzodiazepine-4,10(2H,9H)-dione in 30 ml of dry N,N-dimethylformamide is treated at −40° to −30° with 1.09 g (25 mmol) of sodium hydride (55 percent oil dispersion), the mixture is stirred at the above temperature for a further 50 minutes and 5.3 ml (25 mmol) of phosphoric acid diphenyl ester chloride are subsequently added dropwise thereto at −60°.

Separately, 3 g (26.3 mmol) of potassium t-butylate are dissolved in 8 ml of dry N,N-dimethylformamide, the solution is cooled in an acetone/dry-ice bath, 2.9 ml (26.3 mmol) of ethyl isocyanoacetate are added dropwise thereto and the solution obtained is added dropwise to the above reaction mixture in such a manner that the temperature does not rise above −25°. After completion of the addition the mixture is left to warm to 20°, neutralized by the addition of 1.5 ml of glacial acetic acid and poured into 150 ml of water. The mixture is extracted four times with methylene chloride, the combined organic extracts are washed twice with water, dried over magnesium sulphate and evaporated. The residue is chromatograhed on silica gel while eluting with ethyl acetate and subsequently recrystallized from ethyl acetate/n-hexane. There is obtained ethyl (S)-12,12a-dihydro-9-oxo-8-(trifluoromethyl)-9H,11H-azeto[2,1-c]imidazo[1,5-a][1,4]benzodiazepine-1-carboxylate of melting point 183°–184°.

(b) A mixture of 4.44 g (12.2 mmol) of ethyl (S)-12,12a-dihydro-9-oxo-8-(trifluoromethyl)-9H,11H-azeto[2,1-c]imidazo[1,5-a][1,4]benzodiazepine-1-carboxylate, 0.556 g (13.9 mmol) of sodium hydroxide, 18 ml of ethanol and 9 ml of water is heated to boiling under reflux for 1 hour. The ethanol is then distilled off in vacuo and the residue is diluted with 25 ml of water. The mixture is neutralized by the addition of 13.9 ml (13.9 mmol) of 1N hydrochloric acid, the mixture is cooled to about 0°, the product is filtered off under suction, rinsed with water and dried at 90° in a high vacuum. There is obtained (S)-12,12a-dihydro-9-oxo-8-(trifluoromethyl)-9H,11H-azeto[2,1-c]imidazo[1,5-a][1,4]benzodiazepine-1-carboxylic acid of decomposition point 227°–228°.

(c) A solution of 3.5 g (10.4 mmol) of (S)-12,12a-dihydro-9-oxo-8-(trifluoromethyl)-9H,11H-azeto[2,1-c]imidazo[1,5-a][1,4]benzodiazepine-1-carboxylic acid in 15 ml of N,N-dimethylformamide is treated portionwise with 2.36 g (14 mmol) of 1,1′-carbonyldiimidazole and the mixture is stirred at room temperature for 1 hour and at 50° for 0.75 hour. The mixture is then poured into 40 ml of water and extracted four times with methylene chloride. The combined organic extracts are washed twice with water, dried over magnesium sulphate and evaporated. The residue is crystallized by means of ethyl acetate/diethyl ether. There is obtained 1-[[(S)-12,12a-dihydro-9-oxo-8-(trifluoromethyl)-9H,11H-azeto[2,1-c]imidazo[1,5-a][1,4]benzodiazepin-1-yl]carbonyl]imidazole of decomposition point 216°–218°.

(d) A mixture of 2.1 g (5.4 mmol) of 1-[[(S)-12,12a-dihydro-9-oxo-8-(trifluoromethyl)-9H,11H-azeto[2,1-c]imidazo[1,5-a][1,4]benzodiazepin-1-yl]carbonyl]imidazole, 0.48 g (6.5 mmol) of acetamidoxime and 15 ml of N,N-dimethylformamide is stirred at 60° for 1.5 hours. The mixture is then poured into 40 ml of water and extracted four times with methylene chloride. The organic extracts are washed twice with water, dried over magnesium sulphate and evaporated. There is obtained O-[[(S)-12,12a-dihydro-9-oxo-8-(trifluoromethyl)-9H,11H-azeto[2,1-c]imidazo[1,5-a][1,4]benzodiazepin-1-yl]carbonyl]acetamidoxime. For analytical purposes 0.4 g of the crude product is chromatographed on silica gel while eluting with methylene chloride/methanol (9:1). After subsequent recrystallization from ethyl acetate there is obtained the above substance with a decomposition point of 233°.

(e) A mixture of 1.7 g (4.3 mmol) of crude O-[[(S)-12,12a-dihydro-9-oxo-8-(trifluoromethyl)-9H,11H-azeto[2,1-c]imidazo[1,5-a][1,4]benzodiazepin-1-yl]carbonyl]acetamidoxime and 10 ml of glacial acetic acid is stirred at 90° for 1 hour and at 120° for 1.5 hours. The mixture is then evaporated in vacuo and the residue is chromatographed on silica gel while eluting with ethyl acetate. After subsequent recrystallization from methylene chloride/ethyl acetate there is obtained (S)-12,12a-dihydro-1-(3-methyl-1,2,4-oxadiazol-5-yl)-8-(trifluoromethyl)-9H,11H-azeto[2,1-c]imidazo[1,5-a][1,4]benzodiazepin-9-one of melting point 255°–256°.

EXAMPLE 10

(a) 14.53 g (89.6 mmol) of N,N′-carbonyldiimidazole are introduced portion wise into a suspension of 20 g (66.4 mmol) of (S)-7-fluoro-11,12,13,13a-tetrahydro-9-oxo-9H-imidazo[1,5-a]pyrrolo[2,1-c][1,4]benzodiazepine-1-carboxylic acid in 70 ml of N,N-dimethylformamide. The solution obtained is stirred at room temperature and at 50°, in each case for 1 hour, and is then poured into about 300 ml of water. After stirring for 20 minutes the suspension obtained is suction filtered and the residue is washed with water. After drying at 90° for 16 hours in a water-jet vacuum there is obtained 1-[[(S)-7-fluoro-11,12,13,13a-tetrahydro-9-oxo-9H-imidazo[1,5-a]pyrrolo[2,1-c][1,4]benzodiazepin-1-yl]carbonyl]imidazole of melting point 206°–207°.

(b) 20 g (57 mmol) of 1-[[(S)-7-fluoro-11,12,13,13a-tetrahydro-9-oxo-9H-imidazo[1,5-a]pyrrolo[2,1-c][1,4]benzodiazepin-1-yl]carbonyl]imidazole are suspended in 55 ml of N,N-dimethylformamide, the suspension is treated with 9.9 ml of 25 percent ammonia solution in water, the mixture is stirred for a half hour and then poured into 300 ml of water. The precipitated product is filtered off under suction, washed with water and dried at 80° for 48 hours in a water-jet vacuum. There is obtained (S)-7-fluoro-11,12,13,13a-tetrahydro-9-oxo-9H-imidazo[1,5-a]pyrrolo[2,1-c][1,4]benzodiazepine-1-carboxamide of melting point 239°–240°.

(c) 7 g (23.3 mmol) of (S)-7-fluoro-11,12,13,13a-tetrahydro-9-oxo-9H-imidazo[1,5-a]pyrrolo[2,1-c][1,4]benzodiazepine-1-carboxamide and 9.31 g (70 mmol) of N,N-dimethylacetamide dimethyl acetal in 15 ml of N,N-dimethylformamide are stirred at 110° for 2 hours. By dilution with about 20 ml of toluene and 20 ml of ether and cooling to 0° there crystallizes out (R,S)-N-[1-(dimethylamino)ethylidene]-7-fluoro-11,12,13,13a-tetrahydro-9-oxo-9H-imidazo[1,5-a]pyrrolo[2,1-c][1,4]benzodiazepine-1-carboxamide of melting point 224°–225°.

(d) 3.50 g (9.5 mmol) of (R,S)-N-[1-(dimethylamino)ethylidene]-7-fluoro-11,12,13,13a-tetrahydro-9-oxo-9H-imidazo[1,5-a]pyrrolo[2,1-c][1,4]benzodiazepine-1-carboxamide, 3.44 ml of water, 3.44 ml (13.7 mmol) of 4N sodium hydroxide, 14 ml of dioxan, 0.93 g (13.3 mmol) of hydroxylamine hydrochloride and 18 ml of glacial acetic acid are stirred together at 80° for 50 minutes. The yellow solution obtained is poured into 50 ml of water and the resulting suspension is cooled. The precipitated product is filtered off under suction, washed with water and dried. After chromatography on silica gel and subsequent recrystallization from ethyl acetate there is obtained (R,S)-7-fluoro-11,12,13,13a-tetrahydro-1-(3-methyl-1,2,4-oxadiazol-5-yl)-9H-imidazo[1,5-a]pyrrolo[2,1-c][1,4]benzodiazepin-9-one of melting point 226°–227°.

EXAMPLE 11

(a) A mixture of 6.32 g (20 mmol) of (S)-8-chloro-11,12,13,13a-tetrahydro-9-oxo-9H-imidazo[1,5-a]pyrrolo[2,1-c][1,4]benzodiazepine-1-carboxamide, 5.68 g (14 mmol) of 2,4-bis(p-methoxyphenyl)-1,3,2,4-dithiadiphosphetane-2,4-disulphide and 100 ml of toluene is heated to boiling under reflux for 4.5 hours. The solution obtained is then evaporated in vacuo and the residue is chromatographed on silica gel while eluting with ethyl acetate. After recrystallization from methylene chloride/ethyl acetate there is obtained (S)-8-chloro-11,12,13,13a-tetrahydro-9-oxo-9H-imidazo[1,5-a]pyrrolo[2,1-c][1,4]benzodiazepine-1-carbonitrile of melting point 237°–238°.

(b) 7.0 g (23.4 mmol) of (S)-8-chloro-11,12,13,13a-tetrahydro-9-oxo-9H-imidazo[1,5-a]pyrrolo[2,1-c][1,4]benzodiazepine-1-carbonitrile are stirred at boiling temperature for 1.5 hours together with about 1.0 g of freshly prepared hydroxylamine in 90 ml of ethanol. By cooling, filtering off the precipitated material, washing with ether and drying there is obtained (S)-8-chloro-11,12,13,13a-tetrahydro-9-oxo-9H-imidazo[1,5-a]pyrrolo[2,1-c][1,4]benzodiazepine-1-carboxamidoxime of melting point 249°–250°. By chromatography of the residue from the mother liquor on silica gel and subsequent crystallization from ethyl acetate there is obtained a second portion of the desired amidoxime.

(c) 3.31 g (10 mmol) of (S)-8-chloro-11,12,13,13a-tetrahydro-9-oxo-9H-imidazo[1,5-a]pyrrolo[2,1-c][1,4]benzodiazepine-1-carboxamidoxime are introduced portionwise at room temperature and within 5 minutes into 15 ml of acetic anhydride. The mixture is stirred at room temperature for 1 hour, the acetic anhydride is distilled off and the residue is heated to 140° for 1.5 hours. After two-fold recrystallisation from methylene chloride/ethyl acetate there is obtained (S)-O-acetyl-8-chloro-11,12,13,13a-tetrahydro-9-oxo-9H-imidazo[1,5-a]pyrrolo[2,1-c][1,4]benzodiazepine-1-carboxamidoxime of decomposition point 217°.

(d) 2.42 g (6.5 mmol) of (S)-O-acetyl-8-chloro-11,12,13,13a-tetrahydro-9-oxo-9H-imidazo[1,5-a]pyrrolo[2,1-c][1,4]benzodiazepine-1-carboxamidoxime are treated with 50 ml of glacial acetic acid, whereupon the mixture is stirred at boiling temperature for 1.5 hours. The glacial acetic acid is distilled off and the residue is chromatographed on silica gel while eluting with chloroform which contains 5% methanol. After recrystallization from ethyl acetate/n-hexane there is obtained (S)-8-chloro-11,12,13,13a-tetrahydro-1-(5-methyl-1,2,4-oxadiazol-3-yl)-9H-imidazo[1,5-a]pyrrolo[2,1-c][1,4]benzodiazepin-9-one of melting point 205°–206°.

EXAMPLE 12

(a) 5.0 g of 1-[[(S)-8-chloro-11,12,13,13a-tetrahydro-9-oxo-9H-imidazo[1,5-a]pyrrolo[2,1-c][1,4]benzodiazepin-1-yl]carbonyl]imidazole are stirred at 70° for 1 hour together with 2 g of isobutyramidoxime in 30 ml of N,N-dimethylformamide. The mixture is poured into 250 ml of water and extracted four times with 40 ml of methylene chloride each time. The combined organic phases are washed with water, dried over magnesium sulphate and evaporated. There is obtained O-[[(S)-8-chloro-11,12,13,13a-tetrahydro-9-oxo-9H-imidazo[1,5-a]pyrrolo[2,1-c][1,4]benzodiazepin-1-yl]carbonyl]isobutyramidoxime of melting point 220°–221°.

(b) 4.5 g (11.2 mmol) of O-[[(S)-8-chloro-11,12,13,13a-tetrahydro-9-oxo-9H-imidazo[1,5-a]pyrrolo[2,1-c][1,4]benzodiazepin-1-yl]carbonyl]isobutyramidoxime are stirred at 110° for 1 hour together with 20 ml of glacial acetic acid. The mixture is evaporated and the residue is chromatographed on silica gel while eluting with chloroform which contains 5% methanol. After recrystallization from ethyl acetate there is obtained (S)-8-chloro-11,12,13,13a-tetrahydro-1-(3-isopropyl-1,2,4-oxadiazol-5-yl)-9H-imidazo[1,5-a]pyrrolo[2,1-c][1,4]benzodiazepin-9-one of melting point 187°–188°.

EXAMPLE 13

(a) 19 g (60 mmol) of (S)-8-chloro-11,12,13,13a-tetrahydro-9-oxo-9H-imidazo[1,5-a]pyrrolo[2,1-c][1,4]benzodiazepine-1-carboxamide are suspended in 110 ml of N,N-dimethylformamide, whereupon the suspension is treated with 17 ml (116 mmol) of N,N-dimethylacetamide dimethyl acetal and the mixture is stirred at 115° for 2.5 hours. The mixture is then cooled to 0°, the product is filtered off under suction, rinsed with N,N-dimethylformamide and diethyl ether and dried at 80° in a high vacuum. There is obtained (S)-8-chloro-N-[1-(dimethylamino)ethylidene]-11,12,13,13a-tetrahydro-9-oxo-9H-imidazo[1,5-a]pyrrolo[2,1-c][1,4]benzodiazepine-1-carboxamide of decomposition point 289°–291°.

(b) A mixture of 3.96 g (10.3 mmol) of (S)-8-chloro-N-[1-(dimethylamino)ethylidene]-11,12,13,13a-tetrahydro-9-oxo-9H-imidazo[1,5-a]pyrrolo[2,1-c][1,4]benzodiazepine-1-carboxamide, 25 ml of glacial acetic acid and 0.65 ml (12.4 mmol) of methylhydrazine is stirred at 90° for 1.75 hours. The solution is then evaporated in vacuo and the residue is chromatographed on silica gel while eluting with ethyl acetate/methanol (19:1). After recrystallization from methylene chloride/ethyl acetate there is obtained (S)-8-chloro-1-(1,3-dimethyl-1H-1,2,4-triazol-5-yl)-11,12,13,13a-tetrahydro-9H-imidazo[1,5-a]pyrrolo[2,1-c][1,4]benzodiazepin-9-one of melting point 221°–222°.

EXAMPLE 14

A mixture of 1.5 g (3.9 mmol) of (S)-8-chloro-N-[1-(dimethylamino)ethylildene]-11,12,13,13a-tetrahydro-9-oxo-9H-imidazo[1,5-a]pyrrolo[2,1-c][1,4]benzodiazepine-1-carboxlamide, 10 ml of glacial acetic acid and 0.22 ml (about 7 mmol) of hydrazine hydrate (99 percent) is stirred at 90° for 1.5 hours. The solution is then evaporated in vacuo and the residue is chromatographed on silica gel while eluting with methylene chloride/methanol (9:1). After recrystallization from methanol/diethyl ether there is obtained (S)-8-chloro-11,12,13,13a-tetrahydro-1-(5-methyl-1H-1,2,4-triazol-3-yl)-9H-imidazol[1,5-a]-pyrrolo[2,1-c][1,4]benzodiazepin-9-one of decomposition point 271°–273°.

EXAMPLE 15

1.75 g (5.3 mmol) of (S)-8-chloro-11,12,13,13a-tetrahydro-9-oxo-9H-imidazo[1,5-a]pyrrolo[2,1- c][1,4]benzodiazepine-1-carboxamidoxime are treated with 10 ml of isobutyric anhydride and the mixture is stirred at room temperature for 40 minutes. 14 ml of glacial acetic acid are then added to the mixture (which contains the (S) compound of formula II, wherein Q signifies the group —C(NH$_2$)=NOCOCH(CH$_3$)$_2$, R$^2$ and R$^3$ together signify trimethylene, R$^4$ signifies chlorine and R$^5$ signifies hydrogen) and the mixture is stirred at 120° for 4 hours. The reaction mixture is evaporated in a high vacuum and the residue is chromatographed on silica gel while eluting with ethyl acetate. After recrystallization from ethyl acetate/n-hexane there is obtained (S)-8-chloro-11,12,13,13a-tetrahydro-1-(5-isopropyl-1,2,4-oxadiazol-3-yl)-9H-imidazo[1,5-a]pyrrolo[2,1-c][1,4]benzodiazepin-9-one of melting point 195°–196°.

EXAMPLE 16

(a) N-(2,4-Dimethoxybenzyl)glycine is prepared by reacting glycine with 2,4-dimethoxybenzaldehyde in the presence of sodium hydroxide, reducing with palladium-on-carbon in methanol and subsequently neutralizing with 2N hydrochloric acid. The aqueous solution obtained is concentrated. 18.6 g of the mixture of N-(2,4-dimethoxybenzyl)glycine and sodium chloride obtained are stirred at 80° and 90°, in each case for 1 hour, together with 60 ml of N,N-dimethylformamide and 10 g (50.6 mmol) of 6-chloroisatoic anhydride. The reaction mixture is evaporated and the residue is heated at 135°–140° for 5 hours in a high vacuum. The crystalline product is boiled in 90 ml of N,N-dimethylformamide, whereupon the mixture is poured into 400 ml of hot water. The mixture is left to cool to room temperature while stirring, then cooled to about 0° in an ice-bath, the product is filtered off under suction, rinsed with water and the material obtained is dissolved in 20 ml of hot N,N-dimethylformamide. After the addition of 150 ml of ethyl acetate the mixture is left to stand in an ice-bath for 1 hour, the product is filtered off under suction, rinsed with cold ethyl acetate and dried at 80° in vacuo. There is obtained 6-chloro-4-(2,4-dimethoxybenzyl)-3,4-dihydro-2H-1,4-benzodiazepine-2,5(1H)-dione of melting point 230°–231°.

(b) A suspension of 12.3 g (282.2 mmol) of sodium hydride (55 percent oil dispersion) in 400 ml of dry N,N-dimethylformamide is treated at −20° to −10° while stirring with 107.2 g (297.1 mmol) of 6-chloro-4-(2,4-dimethoxybenzyl)-3,4-dihydro-2H-1,4-benzodiazepine-2,5(1H)-dione, the mixture is stirred at the above temperature for a further 45 minutes and 60 ml (282.2 mmol) of phosphoric acid diphenyl ester chloride are subsequently added dropwise thereto at about −57°.

Separately, 34.4 g (297.1 mmol) of potassium t-butylate are dissolved in 70 ml of dry N,N-dimethylformamide, the mixture is cooled in an acetone/dry-ice bath, 32.5 ml (297.1 mmol) of ethyl isocyanoacetate are added dropwise thereto and the solution obtained is added dropwise to the above reaction mixture in such a manner that the temperature does not exceed −25°. The mixture is left to warm to 19°, neutralized with 18 ml of glacial acetic acid, poured into 1.5 l of water and extracted five times with methylene chloride. The organic extracts are washed three times with water, dried over magnesium sulphate and evaporated. The residue is chromatographed on silica gel while eluting with ethyl acetate. After crystallization of the oil obtained by means of ethyl acetate/n-hexane there is obtained ethyl 7-chloro-5-(2,4-dimethoxybenzyl)-5,6-dihydro-6-oxo-4H-imidazo[1,5-a][1,4]benzodiazepine-3-carboxylate of melting point 129°–130°.

(c) 55.6 g (122 mmol) of ethyl 7-chloro-5-(2,4-dimethoxybenzyl-5,6-dihydro-6-oxo-4H-imidazo[1,5-a][1,4]benzodiazepine-3-carboxylate are heated to reflux while stirring for 24 hours together with 180 ml of trifluoroacetic acid. After evaporation in vacuo the residue is treated with about 500 ml of water and made alkaline with solid potassium carbonate. The precipitated material is filtered off under suction, rinsed with water and dried at 80° in a high vacuum. For purification, the crude product is boiled in 300 ml of dioxan, filtered off under suction and again boiled in 250 ml of dioxan. Both mother liquors are then evaporated together to a volume of about 300 ml, left to crystallize at room temperature overnight, the crystals are filtered off under suction and rinsed with diethyl ether. After drying there is obtained ethyl 7-chloro-5,6-dihydro-6-oxo-4H-imidazo[1,5-a][1,4]-benzodiazepine-3-carboxylate of melting point 278°–279°.

(d) A mixture of 9 g (29.4 mmol) of ethyl 7-chloro-5,6-dihydro-6-oxo-4H-imidazo[1,5-a][1,4]benzodiazepine-3-carboxylate, 1.434 g (35.9 mmol) of sodium hydroxide, 30 ml of ethanol and 15 ml of water is heated to boiling under reflux for 70 minutes. The mixture is then diluted with 80 ml of water, filtered, the filtrate is neutralized by the addition of 8.9 ml (35.9 mmol) of 4N hydrochloric acid and the ethanol is distilled off in vacuo. The residue is subsequently cooled to about 0°, the product is filtered off under suction, rinsed with water and dried at 80°–90° in a high vacuum. There is obtained 7-chloro-5,6-dihydro-6-oxo-4H-imidazo[1,5-a][1,4]benzodiazepine-3-carboxylic acid of decomposition point 289°.

(e) A suspension of 7.4 g (26.9 mmol) of 7-chloro-5,6-dihydro-6-oxo-4H-imidazo[1,5-a][1,4]benzodiazepine-3-carboxylic acid in 30 ml of N,N-dimethylformamide is treated with 5.83 g (35 mmol) of 1,1'-carbonyldiimidazole and the mixture is stirred at room temperature for 20 minutes and at 60° for 30 minutes. The mixture is subsequently poured into 150 ml of water, the product is filtered off under suction, rinsed with water and dried at 90° in a high vacuum. There is obtained 1-[[7-chloro-5,6-dihydro-6-oxo-4H-imidazo[1,5-a][1,4]benzodiazepin-3-yl]carbonyl]imidazole of decomposition point 255°–257°.

(f) A mixture of 7 g (21.4 mmol) of 1-[[7-chloro-5,6-dihydro-6-oxo-4H-imidazo[1,5-a][1,4]benzodiazepin-3-yl]carbonyl]imidazole, 1.91 g (25.8 mmol) of acetamidoxime and 45 ml of N,N-dimethylformamide is stirred at 70° for 1.75 hours. The suspension obtained is then poured into 100 ml of water, the product is filtered off under suction after 0.5 hour, rinsed with water and dried at 80°–90° in a high vacuum. There is obtained 0-[[7-chloro-5,6-dihydro-6-oxo-4H-imidazo[1,5-a][1,4]benzodiazepin-3-yl]carbonyl]acetamidoxime of decomposition point 269°–270°.

(g) A suspension of 6.41 g (19.2 mmol) of 0-[[7-chloro-5,6-dihydro-6-oxo-4H-imidazo[1,5-a][1,4]benzodiazepin-3-yl]carbonyl]acetamidoxime in 45 ml of glacial acetic acid is heated to boiling under reflux for 1 hour. The solution obtained is then evaporated in vacuo, the residue is treated with methylene chloride, cooled to about 0°, the insoluble material is filtered off under suction and the mother liquor is evaporated in vacuo. The residue is again treated with methylene chloride, cooled in an ice-bath, filtered off under suction and the thus-obtained material is recrystallized from N,N-dimethylformamide. There is obtained 7-chloro-5,6-dihydro-3-(3-methyl-1,2,4-oxadiazol-5-yl)-4H-imidazo[1,5-a][1,4]benzodiazepin-6-one of decomposition point 295°–296°.

EXAMPLE 17

(a) 33.18 g (100 mmol) of ethyl (S)-8-chloro-12,12a-dihydro-9-oxo-9H,11H-azeto[2,1-c]imidazo[1,5-a][1,4]benzodiazepine-1-carboxylate are stirred at boiling temperature for 4 hours together with 100 ml of hydrazine hydrate in 300 ml of ethanol. The mixture is evaporated to half and left to crystallize over the weekend. The separated material is filtered off under suction, washed with ethanol and ether and there is obtained after drying (S)-8-chloro-12,12a-dihydro-9-oxo-9H,11H-azeto [2,1-c]imidazo[1,5-a][1,4]benzodiazepine-1-carboxyhydrazide of melting point 215°–217°.

(b) 13.0 g (41 mmol) of (S)-8-chloro-12,12a-dihydro-9-oxo-9H,11H-azeto [2,1-c]imidazo[1,5-a][1,4]benzodiazepine-1-carboxyhydrazide are heated to boiling under reflux for 1 hour together with 70 ml (400 mmol) of triethyl orthoacetate in 350 ml of ethanol. The mixture is then concentrated to about 100 ml, diluted with 100 ml of ethyl acetate and cooled in an ice-bath. By filtering off the precipitated product under suction and washing with ethyl acetate there is obtained (S)-N'-[(E/Z)-1-ethoxyethylidene]-8-chloro-12,12a-dihydro-9-oxo-9H,11H-azeto [2,1-c]imidazo[1,5-a][1,4]benzodiazepine-1-carboxyhydrazide of melting point of 255°–256°.

(c) 5.80 g (15 mmol) of (S)-N'-[(E/Z)-1-ethoxyethylidene]-8-chloro-12,12a-dihydro-9-oxo-9H,11H-azeto[2,1-c]imidazo[1,5-a][1,4]benzodiazepine-1-carboxyhydrazide are stirred at boiling temperature overnight together with 5 ml of 1,8-diazabicyclo[5.4.0]undec-7-ene and 300 ml of N,N-dimethylformamide. The reaction mixture is evaporated to dryness and the residue is dissolved in methylene chloride. The solution is washed with water, dried over magnesium sulphate and evaporated. After recrystallization from methylene chloride and ethyl acetate there is obtained (R,S)-8-chloro-12,12a-dihydro-1-(5-methyl-1,3,4-oxadiazol-2-yl)-9H,11H-azeto[2,1-c]imidazo[1,5-a][1,4]benzodiazepin-9-one of melting point 239°–240°.

EXAMPLE 18

(a) 10 g (31.5 mmol) of (S)-8-chloro-12,12a-dihydro-9-oxo-9H,11H-azeto[2,1-c]imidazo[1,5-a][1,4]benzodiazepine-1-carboxyhydrazide and 70 ml (420 mmol) of ethyl orthoformate are heated to boiling under reflux for 1 hour together with 500 ml of ethanol. The mixture is concentrated to about 100 ml and cooled to 0°. The precipitated product is filtered off under suction and washed with cold ethanol. After drying there is obtained (S)-N'-[(E/Z)-ethoxymethylidene]-8-chloro-12,12a-dihydro-9-oxo-9H,11H-azeto[2,1-c]imidazo[1,5-a][1,4]benzodiazepine-1-carboxyhydrazide of melting point 237°–238°.

(b) 4.6 g (12.3 mmol) of (S)-N'-[(E/Z)-ethoxymethylidene]-[chloro-12,12a-dihydro-9-oxo-9H,11H-azeto[2,1-c]imidazo[1,5-a][1,4]benzodiazepine-1-carboxyhydrazide, 300 ml of n-butanol and 5 ml of 1,8-diazabicyclo[5.4.0]undec-7-ene are heated together to boiling under reflux for 5 hours. The reaction mixture is evaporated and the residue is recrystallized twice from ethyl acetate. There is obtained (S)-8-chloro-12,12a-dihydro-1-(1,3,4-oxadiazol-2-yl)-9H,11H-azeto[2,1-c]imidazo[1,5-a][1,4]benzodiazepin-9-one of melting point 264°–265°.

EXAMPLE 19

(a) 34.6 g (100 mmol) of ethyl (S)-8-chloro-11,12,13,13a-tetrahydro-9-oxo-9H-imidazo[1,5-a]pyrrolo[2,1-c][1,4]benzodiazepine-1-carboxylate, 100 ml of hydrazine hydrate and 100 ml of ethanol are heated to boiling under reflux for 16 hours. The mixture is concentrated to about 150 ml and cooled. The product which crystallizes out is filtered off under suction and washed with ether. After recrystallization from dioxan there is obtained (S)-8-chloro-11,12,13,13a-tetrahydro-9-oxo-9H-imidazo[1,5-a]pyrrolo[2,1-c][1,4]benzodiazepine-1-carboxyhydrazide of melting point 265°–267°.

(b) 5.0 g (15 mmol) of (S)-8-chloro-11,12,13,13a-tetrahydro-9-oxo-9H-imidazo[1,5-a]pyrrolo[2,1-c][1,4]benzodiazepine-1-carboxyhydrazide are stirred at boiling temperature for 1 hour together with 50 ml of ethyl orthoformate and 500 ml of ethanol. By evaporation of the solution and crystallization of the residue from ethyl acetate there is obtained (S)-N'-[(E/Z)-ethoxymethylidene]-8-chloro-11,12,13,13a-tetrahydro-9-oxo-9H-imidazo[1,5-a]pyrrolo[2,1-c][1,4]benzodiazepine-1-carboxyhydrazide of melting point 223°–224°.

(c) 4.0 g (10.3 mmol) of (S)-N'-[(E/Z)-ethoxymethylidene]-8-chloro-11,12,13,13a-tetrahydro-9-oxo-9H-imidazo[1,5-a]pyrrolo[2,1-c][1,4]benzodiazepine-1-carboxyhydrazide are stirred at boiling temperature for 4 hours together with 5 ml of 1,8-diazabicyclo[5.4.0]undec-7-ene and 300 ml of n-butanol. The mixture is evaporated and the residue is chromatographed on silica gel while eluting with chloroform which contains 5% methanol. By recrystallization from ethanol there is obtained (S)-8-chloro-11,12,13,13a-tetrahydro-1-(1,3,4-oxadiazol-2-yl)-9H-imidazo[1,5-a]pyrrolo[2,1-c][1,4]benzodiazepin-9-one of melting point 229°–230°.

EXAMPLE 20

(a) 6.61 g (20 mmol) of (S)-8-chloro-11,12,13,13a-tetrahydro-9-oxo-9H-imidazo[1,5-a]pyrrolo[2,1-c][1,4]benzodiazepine-1-carboxyhydrazide are stirred at boiling temperature for 1.5 hours together with 40 ml of triethyl orthoacetate and 200 ml of ethanol. The solution is concentrated to about 30 ml and diluted with 30 ml of ethyl acetate. By filtering off the precipitated product under suction, washing with ethyl acetate and drying there is obtained (S)-N'-[(E/Z)-1-ethoxyethylidene]-8-chloro-11,12,13,13a-tetrahydro-9-oxo-9H-imidazo[1,5-a]pyrrolo[2,1-c][1,4]benzodiazepine-1-carboxyhydrazide of melting point 252°–254°.

(b) 5.10 g (12.7 mmol) of (S)-N'-[(E/Z)-1-ethoxyethylidene]-8-chloro-11,12,13,13a-tetrahydro-9-oxo-9H-imidazo[1,5-a]pyrrolo[2,1-c][1,4]benzodiazepine-1-carboxyhydrazide are heated to boiling under reflux overnight together with 5 ml of 1,8-diazabicyclo[5.4.0]undec-7-ene and 250 ml of N,N-dimethylformamide. The reaction mixture is evaporated, the residue is dissolved in methylene chloride, the organic phase is washed with water, dried over magnesium sulphate and evaporated. After recrystallization from methylene chloride/ethyl acetate there is obtained (S)-8-chloro-11,12,13,13a-tetrahydro-1-(5-methyl-1,3,4-oxadiazol-2-yl)-9H-imidazo[1,5-a]pyrrolo[2,1-c][1,4]benzodiazepin-9-one of melting point 253°–254°.

EXAMPLE 21

(a) 9.95 g (30 mmol) of (S)-8-chloro-11,12,13,13a-tetrahydro-9-oxo-9H-imidazo [1,5-a]pyrrolo[2,1-c][1,4]benzodiazepine-1-carboxyhydrazide are heated to boiling under reflux for 2 hours together with 35 ml of triethyl orthopropionate and 200 ml of ethanol. The mixture is evaporated to half, diluted with 50 ml of ethyl acetate and cooled in an ice-bath. By filtering off the precipitated product under suction and drying there is obtained (S)-N'-[(E/Z)-1-ethoxypropylidene]-8-chloro-11,12,13,13a-tetrahydro-9-oxo-9H-imidazo [1,5-a]pyrrolo[2,1-c][1,4]benzodiazepine-1-carboxyhydrazide of melting point 251°–252°.

(b) 6.0 g (15 mmol) of (S)-N'-[(E/Z)-1-ethoxypropylidene]-8-chloro-11,12,13,13a-tetrahydro-9-oxo-9H-imidazo[1,5-a]pyrrolo[2,1-c][1,4]benzodiazepine-1-carboxyhydrazide are stirred at 135° overnight together with 5 ml of 1,8-diazabicyclo[5.4.0]undec-7-ene and 200 ml of N,N-dimethylformamide. The solution is evaporated and the residue is dissolved in methylene chloride. The solution is washed twice with water, dried over magnesium sulphate and evaporated. After two-fold recrystallization from methylene chloride/ethyl acetate there is obtained (S)-8-chloro-1-(5-ethyl-1,3,4-oxadiazol-2-yl)-11,12,13,13a-tetrahydro-9H-imidazo[1,5-a]pyrrolo[2,1-c]benzodiazepin-9-one of melting point 220°–221°.

EXAMPLE 22

(a) 9.95 g (30 mmol) of (S)-8-chloro-11,12,13,13a-tetrahydro-9-oxo-9H-imidazo[1,5-a]pyrrolo[2,1-c][1,4]benzodiazepine-1-carboxyhydrazide are heated to boiling under reflux for 10 hours together with 35 ml of triethyl orthobenzoate and 200 ml of ethanol. By evaporation of the solution and recrystallization of the residue from ethyl acetate there is obtained (S)-N'-[(E/Z)-α-ethoxybenzylidene]-8-chloro-11,12,13,13a-tetrahydro-9-oxo-9H-imidazo[1,5-a]pyrrolo[2,1-c][1,4]benzodiazepine-1-carboxyhydrazide.

(b) 5 g (10.8 mmol) of (S)-N'-[(E/Z)-α-ethoxybenzylidene]-8-chloro-11,12,13,13a-tetrahydro-9-oxo-9H-imidazo[1,5-a]pyrrolo[2,1-c][1,4]benzodiazepine-1-carboxyhydrazide are stirred at boiling temperature overnight together with 230 ml of n-butanol and 5 ml of 1,8-diazabicyclo[5.4.0]undec-7-ene. The mixture is evaporated to dryness, the residue is taken up in methylene chloride and washed twice with water. By drying over magnesium sulphate, evaporation and recrystallization from ethyl acetate there is obtained (S)-8-chloro-11,12,13,13a-tetrahydro-1-(5-phenyl-1,3,4-oxadiazol-2-yl)-9H-imidazo[1,5-a]pyrrolo [2,1-c][1,4]benzodiazepin-9-one of melting point 221°–222°.

EXAMPLE 23

(a) A suspension of 13.3 g (40 mmol) of ethyl (S)-8-chloro-12,12a-dihydro-9-oxo-9H,11H-azeto[2,1-c]imidazo[1,5-a][1,4]benzodiazepine-1-carboxylate in 85 ml of tetrahydrofuran is heated to 50° and a suspension of 1.06 g (48.7 mmol) of lithium borohydride in 15 ml of tetrahydrofuran is then added dropwise to the solution obtained. The white suspension is subsequently heated to boiling under reflux for 70 minutes. The mixture is cooled to 20° and 54 ml of a solution consisting of 27 ml of conc. hydrochloric acid and 27 ml of water is added dropwise thereto. The tetrahydrofuran is distilled off in vacuo and the aqueous residue is made alkaline with 25 percent ammonia. The mixture is left to crystallize in an ice-bath for 1 hour, the precipitated material is filtered off under suction, rinsed with water and dried at 80° in a high vacuum. There is obtained (S)-8-chloro-12,12a-dihydro-1-(hydroxymethyl)-9H,11H-azeto[2,1-c]imidazo[1,5-a][1,4]benzodiazepin-9-one of decomposition point 256°–258°.

(b) A mixture of 8.96 g (30.9 mmol) of (S)-8-chloro-12,12a-dihydro-1-(hydroxymethyl)-9H,11H-azeto[2,1-c]imidazo[1,5-a][1,4]benzodiazepin-9-one, 35 g of manganese (IV) oxide and 150 ml of methylene chloride is stirred at room temperature for 2 hours. The mixture is filtered under suction over Dicalit, the residue is rinsed with methylene chloride and the filtrate is evaporated. After recrystallization from methylene chloride/ethyl acetate there is obtained (S)-8-chloro-12,12a-dihydro-9-oxo-9H,11H-azeto [2,1-c]imidazo[1,5-a][1,4]benzodiazepine-1-carboxyaldehyde of melting point 210°–211°.

(c) A solution of 1.44 g (5 mmol) of sodium carbonate.10H$_2$O in 20 ml of water is added dropwise to a mixture of 2.09 g (7.3 mmol) of (S)-8-chloro-12,12a-dihydro-9-oxo-9H,11H-azeto [2,1-c]imidazo[1,5-a][1,4]benzodiazepine-1-carboxyaldehyde, 0.78 g (9.3 mmol) of O-methylhydroxylamine hydrochloride and 65 ml of water and the mixture is stirred at room temperature for 3 hours. The mixture is then suction filtered, the material on the suction filter is washed with water and taken up in methylene chloride, the solution is dried over magnesium sulphate and evaporated. The residue is chromatographed on silica gel while eluting with ethyl acetate. After recrystallization from ethyl acetate/n-hexane there is obtained (S)-8-chloro-12,12a-dihydro-9-oxo-9H,11H-azeto[2,1-c]imidazo[1,5-a][1,4]benzodiazepine-1-carboxaldehyde O-methyl oxime of melting point 199°–200°.

EXAMPLE 24

(a) A suspension of 81.2 g (234.8 mmol) of ethyl (S)-8-chloro-11,12,13,13a-tetrahydro-9-oxo-9H-imidazo[1,5-a]pyrrolo[2,1-c][1,4]benzodiazepine-1-carboxylate in 450 ml of dry tetrahydrofuran is heated to about 50° and a suspension of 6.1 g (279 mmol) of lithium borohydride in 60 ml of tetrahydrofuran is added dropwise to the solution obtained. The suspension is subsequently heated to boiling under reflux for 3 hour. The mixture is cooled to room temperature and there are added dropwise thereto firstly 40 ml of 3N hydrochloric acid and then 260 ml of a solution consisting of 130 ml of conc. hydrochloric acid and 130 ml of water. The solution obtained is stirred at 40° for 15 minutes, the tetrahydrofuran is distilled off in vacuo and the aqueous residue is made alkaline with 25 percent ammonia. The precipitated material is then filtered off under suction, washed with water and dried at 80° in high vacuum. There is obtained (S)-8-chloro-11,12,13,13a-tetrahydro-1-(hydroxymethy)-9H-imidazo[1,5-a]pyrrolo[2,1-c][1,4]benzodiazepin-9-one of melting point 303°–305°.

(b) A mixture of 15.2 g (50 mmol) of (S)-8-chloro-11,12,13,13a-tetrahydro-1-(hydroxymethyl)-9H-imidazo[1,5-a]pyrrolo[2,1-c][1,4]benzodiazepin-9-one, 60 g of manganese (IV) oxide and 300 ml of methylene chloride is stirred at room temperature for 1.5 hours. The mixture is suction filtered over Dicalit, the residue is rinsed with methylene chloride and the filtrate is evaporated. After recrystallization from methylene chloride/ethyl acetate there is obtained (S)-8-chloro-11,12,13,13a-tetrahydro-9-oxo-9H-imidazo [1,5-a]pyrrolo[2,1-c][1,4]benzodiazepine-1-carboxaldehyde of melting point 224°–225°.

(c) A solution of 4.3 g (15 mmol) of sodium carbonate.10H$_2$O in 30 ml of water is added dropwise to a mixture of 3.62 g (12 mmol) of (S)-8-chloro-11,12,13,13a-tetrahydro-9-oxo-9H-imidazo[1,5-a]pyrrolo[2,1-c][1,4]benzodiazepine-1-carboxyaldehyde, and 1.88 g (15 mmol) of O-t-butylhydroxylamine hydrochloride in 50 ml of water and the mixture is then stirred to room temperature for a further 1 hour. The mixture is then suction filtered, the material on the suction filter is washed with water and taken up in methylene chloride, dried over magnesium sulphate and evaporated. The residue is chromatographed on silica gel while eluting with ethyl acetate. After crystallization by means of diethyl ether there is obtained (S)-8-chloro-11,12,13,13a-tetrahydro-9-oxo-9H-imidazo[1,5-a]pyrrolo[2,1-c][1,4]benzodiazepine-1-carboxaldehyde O-t-butyl oxime of melting point 215°–216°.

EXAMPLE 25

A solution of 4.6 g (16 mmol) of sodium carbonate.10-H$_2$O in 30 ml of water is added dropwise at room temperature to a mixture of 3.62 g (12 mmol) of (S)-8-chloro-11,12,13,13a-tetrahydro-9-oxo-9H-imidazo[1,5-a]pyrrolo[2,1-c][1,4]benzodiazepine-1-carboxaldehyde, 1.34 g (16 mmol) of O-methylhydroxylamine hydrochloride in 45 ml of water and the mixture is then stirred at 70° for 4 hours. The precipitated material is filtered off under suction, washed with water, then taken up in methylene chloride, the methylene chloride phase is dried over magnesium sulphate and evaporated. The residue is chromatographed on silica gel while eluting with chloroform which contains 2% methanol. After recrystallization from ethyl acetate/hexane there is obtained (S)-8-chloro-11,12,13,13a-tetrahydro9-oxo-9H-imidazo[1,5-a]pyrrolo[2,1-c][1,4]benzodiazepine-1-carboxaldehyde O-methyl oxime of melting point 194°–195°.

EXAMPLE 26

3.31 g (10 mmol) of (S)-8-chloro-11,12,13,13a-tetrahydro-9-oxo-9H-imidazo[1,5-a]pyrrolo[2,1-c][1,4]benzodiazepine-1-carboxamidoxime in 10 ml of trifluoroacetic anhydride are stirred at room temperature for 1.5 hours and the reaction mixture is evaporated. By chromatography of the residue on silica gel while eluting with chloroform which contains 5% methanol and subsequent recrystallization from ethyl acetate/hexane there is obtained (S)-8-chloro-11,12,13,13a-tetrahydro-1-[5-(trifluoromethyl)-1,2,4-oxadiazol-3-yl]-9H-imidazo[1,5-a]pyrrolo[2,1-c][1,4]benzodiazepin-9-one of melting point 220°–221°.

EXAMPLE 27

A mixture of 1.51 g (5 mmol) of (S)-8-chloro-11,12,13,13a-tetrahydro-9-oxo-9H-imidazo[1,5-a]pyrrolo[2,1-c][1,4]benzodiazepine-1-carboxaldehyde, 1.07 g (5.5 mmol) of toluene-4-sulphonylmethyl isocyanide, 1 g of powdered potassium carbonate and 20 ml of methanol is heated to boiling under reflux for 2 hours. The mixture is then evaporated to a volume of 5 ml and the material obtained is chromatographed on silica gel while eluting with ethyl acetate/methanol (9:1). After recrystallization from ethyl acetate there is obtained (S)-8-chloro-11,12,13,13a-tetrahydro-1-(5-oxazolyl)-9H-imidazo[1,5-a]pyrrolo[2,1-c][1,4]benzodiazepin-9-one of melting point 201°–202°.

EXAMPLE 28

(a) 35.7 g (118 mmol) of (S)-8-chloro-11,12,13,13a-tetrahydro-9-oxo-9H-imidazo[1,5-a]pyrrolo[2,1-c][1,4]benzodiazepine-1-carboxaldehyde are heated to boiling under reflux for 6 hours together with 9.52 g (137 mmol) of hydroxylamine hydrochloride and 14.6 g (214 mmol) of sodium formate in 178 ml of formic acid. The solution obtained is then poured into 2.5 l of water; the precipitated product is filtered off under suction and rinsed with water. After recrystallization from methylene chloride/ethyl acetate there is obtained (S)-8-chloro-11,12,13,13a-tetrahydro-9-oxo-9H-imidazo[1,5-a]pyrrolo[2,1-c][1,4]benzodiazepine-1-carbonitrile of melting point 236°–237°.

(b) 20.0 g (67 mmol) of (S)-8-chloro-11,12,13,13a-tetrahydro-9-oxo-9H-imidazo[1,5-a]pyrrolo[2,1-c][1,4]benzodiazepine-1-carbonitrile and 10.06 g (134 mmol) of thioacetamide are heated to 90° together with 100 ml of dry N,N-dimethylformamide, whereupon the mixture is saturated with dry hydrogen chloride at this temperature for 5 hours. The mixture is cooled to room temperature and poured into 2.5 l of water. The mixture is neutralized to pH 7 with sodium hydroxide solution and the precipitated product is filtered off under suction. The material on the suction filter is taken up in methylene chloride, insoluble material is filtered off and the filtrate is washed with water, dried over magnesium sulphate and concentrated in half. By suction filtration and recrystallization from ethyl acetate there is obtained (S)-8-chloro-11,12,13,13a-tetrahydro-9-oxo-9H-imidazo[1,5-a]pyrrolo[2,1-c][1,4]benzodiazepine-1-carbothioamide of melting point 247°–248°.

(c) 1.66 g (5 mmol) of (S)-8-chloro-11,12,13,13a-tetrahydro-9-oxo-9H-imidazo[1,5-a]pyrrolo[2,1-c][1,4]-benzodiazepine-1-carbothioamide, 0.925 g (10 mmol) of chloroacetone and 25 ml of 1-propanol are heated together to boiling under reflux for 15 hours. The reaction mixture is subsequently evaporated, the residue is dissolved in 50 ml of methylene chloride and the solution is washed with 20 ml of saturated sodium bicarbonate solution. The organic phase is dried over magnesium sulphate, evaporated and the residue is chromatographed while eluting with methylene chloride/ethyl acetate (4:1). After recrystallization from ethyl acetate there is obtained (S)-8-chloro-11,12,13,13a-tetrahydro-1-(4-methyl-2-thiazolyl)-9H-imidazo[1,5-a]pyrrolo[2,1-c]benzodiazepin-9-one of melting point 219°–220°.

EXAMPLE 29

15 g (43.8 mmol) of 1-[[7-chloro-5,6-dihydro-5-methyl-6-oxo-4H-imidazo[1,5-a][1,4]benzodiazepin-3-yl]carbonyl]imidazole, 6.60 g (65.8 mmol) of cyclopropanecarboxamidoxime and 100 ml of N,N-dimethylformamide are stirred at 70° for 1.5 hours, whereupon the mixture is evaporated to dryness, 100 ml of glacial acetic acid are added to the residue and the solution is heated to 120° for 1.5 hours. The solution is then evaporated and the residue is partitioned between methylene chloride and saturated sodium bicarbonate solution. The organic phase is separated, dried over magnesium sulphate and evaporated. By recrystallization of the residue from methylene chloride and ethyl acetate there is obtained 7-chloro-3-(3-cyclopropyl-1,2,4-oxadiazol-5-yl)-5,6-dihydro-5-methyl-4H-imidazo[1,5-a][1,4]benzodiazepin-6-one of melting point 183°–184°.

EXAMPLE 30

15.0 g (42 mmol) of 1-[[(S)-8-chloro-12,12a-dihydro-9-oxo-9H,11H-azeto[2,1-c]imidazo[1,5-a][1,4]benzodiazepin-1-yl]carbonyl]imidazole are dissolved in 60 ml of N,N-dimethylformamide, whereupon the solution is treated with 4.60 g (46 mmol) of cyclopropanecarboxamidoxime and the mixture is heated to 100° for 2 hours.

The mixture is evaporated to dryness, the residue is treated with 50 ml of acetic acid and the mixture is stirred at 115° for 2 hours. After evaporation of the solvent the residue is partitioned between methylene chloride and saturated sodium bicarbonate solution. The organic phase is separated, dried over magnesium sulphate and concentrated. The residue is chromatographed on silica gel while eluting with ethyl acetate. After recrystallization from ethyl acetate there is obtained (S)-8-chloro-1-(3-cyclopropyl-1,2,4-oxadiazol-5-yl)-12,12a-dihydro-9H,11H-azeto[2,1-c]imidazo[1,5-a][1,4]benzodiazepin-9-one of melting point 140°–142°.

EXAMPLE 31

8.10 g (22 mmol) of 1-[[(S)-8-chloro-11,12,13,13a-tetrahydro-9-oxo-9H-imidazo[1,5-a]pyrrolo[2,1-c][1,4]benzodiazepin-1-yl]carbonyl]imidazole are dissolved in 30 ml of N,N-dimethylformamide, whereupon the solution is treated with 2.50 g (25 mmol) of cyclopropanecarboxamidoxime and the mixture is heated to 70° for 4.5 hours. The reaction mixture is then poured into 350 ml of water, stirred for 20 minutes and the precipitated product is filtered off under suction. The residue is washed with water and dried. The above residue is dissolved in 30 ml of glacial acetic acid and stirred at 115° for 2.5 hours. The reaction mixture is subsequently evaporated and the residue is chromatographed on silica gel while eluting with ethyl acetate. After evaporation of the eluate there is obtained (S)-8-chloro-1-(3-cyclopropyl-1,2,4-oxadiazol-5-yl)-11,12,13,13a-tetrahydro-9H-imidazo[1,5-a]pyrrolo[2,1-c][1,4]benzodiazepin-9-one of melting point 213°–214°.

EXAMPLE 32

6.5 g (20 mmol) of 1-[(8-fluoro-5,6-dihydro-5-methyl-6-oxo-4H-imidazo[1,5-a][1,4]benzodiazepin-3-yl)carbonyl]imidazole are stirred at 100° for 1 hour together with 2.2 g (22 mmol) of cyclopropanecarboxamidoxime in 25 ml of N,N-dimethylformamide. The mixture is then evaporated to dryness, 50 ml of glacial acetic acid are added to the residue and the mixture is heated to reflux for 1 hour. The mixture is again evaporated to dryness in vacuo and the residue is dissolved in methylene chloride. The methylene chloride solution is washed twice with sodium bicarbonate solution, subsequently dried with magnesium sulphate and evaporated. By recrystallization from methylene chloride/ethyl acetate there is obtained 3-(3-cyclopropyl-1,2,4-oxadiazol-5-yl)-8-fluoro-5,6-dihydro-5-methyl-4H-imidazo[1,5-a][1,4]benzodiazepin-6-one of melting point 216°–217°.

EXAMPLE 33

A mixture of 8.10 g (22 mmol) of 1-[[(S)-8-chloro-11,12,13,13a-tetrahydro-9-oxo-9H-imidazo[1,5-a]pyrrolo[2,1-c][1,4]benzodiazepin-1-yl]carbonyl]imidazole, 2.60 g (25 mmol) of methoxyacetamidoxime and 30 ml of N,N-dimethylformamide is stirred at 70° for 2.5 hours. The reaction mixture is poured into 300 ml of water, the suspension is suction filtered and the filter residue is rinsed with water and dried at 90° in a high vacuum. Thereupon, 6.55 g of the product obtained are treated with 30 ml of glacial acetic acid and the mixture is stirred at 120° for 4.5 hours. The solution is then evaporated in vacuo and the residue is chromatographed on silica gel while eluting with ethyl acetate. By subsequent recrystallization from ethyl acetate there is obtained (S)-8-chloro-11,12,13,13a-tetrahydro-1-[3-(methoxymethyl)-1,2,4-oxadiazol-5-yl]-9H-imidazo[1,5-a]pyrrolo[2,1-c][1,4]benzodiazepin-9-one of melting point 168°–170°.

EXAMPLE 34

8.60 g (28.5 mmol) of (S)-7-fluoro-11,12,13,13a-tetrahydro-9-oxo-9H-imidazo[1,5-a]pyrrolo[2,1-c][1,4]benzodiazepine-1-carboxylic acid, 30 ml of N,N-dimethylformamide and 6.16 g (38 mmol) of N,N'-carbonyldiimidazole are stirred at room temperature for 45 minutes and at 55° for 1 hour. 2.44 g (33 mmol) of acetamidoxime are subsequently added and the mixture is stirred at 75° for a further 1.5 hours. The mixture is poured into 200 ml of water, stirred for 20 minutes, suction filtered and the filter residue is dried. 8.60 g of the thus-obtained product are stirred at 115° for 2.5 hours in 50 ml of glacial acetic acid. The solution is evaporated and the residue is partitioned between methylene chloride and saturated sodium bicarbonate solution. The organic phase is separated, dried over magnesium sulphate and evaporated. By recrystallization of the residue from ethyl acetate there is obtained (S)-7-fluoro-11,12,13,13a-tetrahydro-1-(3-methyl-1,2,4-oxadiazol-5-yl)-9H-imidazo[1,5-a]pyrrolo[2,1-c][1,4]benzodiazepin-9-one of melting point 248°–249°.

EXAMPLE 35

40 ml of ethanol and 14.0 g (44.9 mmol) of ethyl (S)-11,12,13,13a-tetrahydro-9-oxo-9H-imidazo[1,5-a]pyrrolo[2,1-c][1,4]benzodiazepine-1-carboxylate are added to a solution of 2.21 g (55.2 mmol) of sodium hydroxide in 10 ml of water and the mixture is stirred at boiling temperature for 30 minutes. The mixture is diluted with 40 ml of water and neutralized with 13.8 ml of 4N hydrochloric acid. After evaporation of the ethanol in a water-jet vacuum the suspension is filtered; the filter residue is rinsed with water and dried at 90° in a high vacuum. The product obtained is suspended in 60 ml of N,N-dimethylformamide, 9.40 g (56 mmol) of N,N'-carbonyldiimidazole are added thereto and the mixture is stirred at 60° overnight. The reaction mixture is treated with 3.65 g (49.3 mmol) of acetamidoxime and stirred at 60° for a further 2 hours. The mixture is evaporated to dryness, the residue is dissolved in 50 ml of glacial acetic acid and the solution is heated to 120° for 2.5 hours. The yellow solution is concentrated; the residue is taken up in methylene chloride and washed with a saturated sodium bicarbonate solution. The organic phase is dried over magnesium sulphate, evaporated and there is obtained by recrystallization of the residue from methylene chloride and ethyl acetate (S)-11,12,13,13a-tetrahydro-1-(3-methyl-1,2,4-oxadiazol-5-yl)-9H-imidazo [1,5-a]pyrrolo[2,1-c][1,4]benzodiazepin-9-one of melting point 180°–182°.

EXAMPLE 36

A mixture of 43.64 g (118.65 mmol) of 1-[[(S)-8-chloro-11,12,13,13a-tetrahydro-9-oxo-9H-imidazo[1,5-a]pyrrolo[2,1-c][1,4]benzodiazepin-1-yl]carbonyl]imidazole, 11.5 g (130.5 mmol) of propionamidoxime and 200 ml of N,N-dimethylformamide is stirred at 60° for 2 hours. The cooled suspension is then filtered; the filter residue is rinsed with ether and dried at 70° in a water-jet vacuum. 5.0 g (12.9 mmol) of the product obtained are stirred with 50 ml of glacial acetic acid at 120° for 3 hours. The reaction mixture is evaporated and the residue is dissolved in methylene chloride. The solution is washed with a saturated sodium bicarbonate solution, dried over magnesium sulphate and evaporated. By recrystallization from methylene chloride and ethyl acetate there is obtained (S)-8-chloro-1-(3-ethyl-1,2,4-oxadiazol-5yl)-11,12,13,13a-tetrahydro-9H-imidazo[1,5-a]pyrrolo[2,1-c][1,4]benzodiazepin-9-one of melting point 201–203.

EXAMPLE 37

41.20 g (112.1 mmol) of 1-[[(S)-8-chloro-11,12,13,13a-tetrahydro-9-oxo-9H-imidazo[1,5-a]pyrrolo[2,1-c][1,4]benzodiazepin-1-yl]carbonyl]imidazole and 12.6 g (123.4 mmol) of butyramidoxime are stirred at 60° for 2.5 hours in 200 ml of N,N-dimethylformamide. The cooled suspension is then filtered; the filter residue is rinsed with ether and dried. The product obtained is stirred at 1120° for 3 hours with 350 ml of glacial acetic acid. The reaction mixture is evaporated and the residue is dissolved in methylene chloride. The solution is washed with a saturated sodium bicarbonate solution, dried over magnesium sulphate and evaporated. By recrystallization of the residue from methylene chloride and ethyl acetate there is obtained (S)-8-chloro-11,12,13,13a-tetrahydro-1-(3-propyl-1,2,4-oxadiazol-5-yl)-9H-imidazo[1,5-a]pyrrolo[2,1-c][1,4]-benzodiazepin-9-one of melting point 176°–178°.

EXAMPLE 38

11.0 g (30 mmol) of 1-[[(S)-8-chloro-11,12,13,13a-tetrahydro-9-oxo-9H-imidazo[1,5-a]pyrrolo[2,1-c][1,4]benzodiazepin-1-yl]carbonyl]imidazole are dissolved in 50 ml of N,N-dimethylformamide, whereupon the solution is treated with 3.96 g (34 mmol) of valeramidoxime and the mixture is heated to 85° for 3 hours. The reaction mixture is evaporated to dryness. The residue is dissolved in 50 ml of glacial acetic acid and the mixture is stirred at 110° for 2 hours. The reaction mixture is subsequently evaporated and the residue is chromatographed on silica gel while eluting with ethyl acetate. After evaporation of the eluate there is obtained (S)-1-(3-butyl-1,2,4-oxadiazol-5-yl)-8-chloro-11,12,13,13a-tetrahydro-9H-imidazo[1,5-a]pyrrolo[2,1-c][1,4]benzodiazepin-9-one of melting point 181°–182°.

EXAMPLE 39

A mixture of 39.72 g (108 mmol) of 1-[[(S)-8-chloro-11,12,13,13a-tetrahydro-9-oxo-9H-imidazo[1,5-a]pyrrolo[2,1-c][1,4]benzodiazepin-1-yl]carbonyl]imidazole, 13.8 g (118.8 mmol) of pivalamidoxime and 200 ml of N,N-dimethylformamide is heated to 60° for 3 hours. The reaction mixture is concentrated to dryness; the residue is dissolved in methylene chloride and washed twice with water. The organic phase is dried over magnesium sulphate and evaporated. 45 g (108 mmol) of the product obtained are stirred at 120° for 3 hours with 200 ml of glacial acetic acid. The solution is evaporated and the residue is partitioned between chloroform and saturated sodium bicarbonate solution. The organic phase is separated, dried over magnesium sulphate and concentrated. By recrystallization from methylene chloride and ethyl acetate there is obtained (S)-1-(3-tert.-butyl-1,2,4-oxadiazol-5-yl)-8-chloro-11,12,13,13a-tetrahydro-9H-imidazo[1,5-a]pyrrolo[2,1-c][1,4]benzodiazepin-9-one of melting point 222°–224°.

EXAMPLE 40

17.0 g (105 mmol) of N,N′-carbonyldiimidazole are added portionwise to a solution of 8.61 g (100 mmol) of cyclopropanecarboxylic acid in 30 ml of N,N-dimethylformamide. The mixture is stirred at room temperature for 1 hour and then heated rapidly to 50°. The solution obtained is added to a suspension of 33.1 g (100 mmol) of (S)-8-chloro-11,12,13,13a-tetrahydro-9-oxo-9H-imidazo[1,5-a]pyrrolo[2,1-c][1,4]benzodiazepine-1-carboxamidoxime in 100 ml of N,N-dimethylformamide and the mixture is heated to 90° for 2.5 hours. The solvent is removed on a rotary evaporator and is replaced by 100 ml of acetic acid. After stirring at 120° for 2.5 hours the mixture is again evaporated, the residue is dissolved in methylene chloride and washed with saturated sodium bicarbonate solution. The organic phase is dried over magnesium sulphate and concentrated. By chromatography of the oily residue on silica gel while eluting with ethyl acetate and recrystallization from alcohol and a small amount of methylene chloride there is obtained (S)-8-chloro-1-[5-(cyclopropyl)-1,2,4-oxadiazol-3-yl]-11,12,13,13a-tetrahydro-9H-imidazo[1,5-a]pyrrolo[2,1-c][1,4]benzodiazepin-9-one of melting point 236°–237°

EXAMPLE 41

A solution of 25.07 g (100 ml) of (S)-6-chloro-1,2,3,11a-tetrahydro-5H-pyrrolo[2,1-c][1,4]benzodiazepine-5,11(10H)-dione in 100 ml of dry N,N-dimethylformamide is treated at −30° to −20° with 4.15 g (99 mmol) of sodium hydride (55 percent oil dispersion), the mixture is stirred at the above temperture for a further 50 minutes and subsequently a solution of 19.6 ml (95 mmol) of phosphoric acid diphenyl ester chloride in 15 ml of N,N-dimethylformamide is added dropwise thereto at −65°. The reaction mixture is stirred at −65° for 1 hour and then at this temperature there are added portionwise 11.4 g (100 mmol) of potassium tert.-butylate and subsequently dropwise 10.71 g (100 mmol) of furfuryl isocyanide. After completion of the addition the mixture is left to warm to 10°, neutralized with 9 ml of glacial acetic acid and poured into 700 ml of water. The mixture is extracted four times with methylene chloride, the combined organic extracts are washed twice with water, dried over magnesium sulphate and evaporated. The residue is chromatographed on silica gel while eluting with ethyl acetate and there is obtained after recrystallization from ethyl acetate (S)-8-chloro-11,12,13,13a-tetrahydro-1-(2-furyl)-9H-imidazo[1,5-a]pyrrolo [2,1-c][1,4]benzodiazepin-9-one of melting point 176°–178°.

EXAMPLE 42

(a) A mixture of 54.7 g (148.7 mmol) of 1-[[(S)-8-chloro-11,12,13,13a-tetrahydro-9-oxo-9H-imidazo[1,5-a]pyrrolo[2,1-c][1,4]benzodiazepin-1-yl]carbonyl]imidazole, 100 ml of N,N-dimethylformamide and 8.60 g (156.1 mmol) of propargylamine is stirred at room temperature overnight. The solution obtained is then poured into 500 ml of water, the resulting suspension is filtered under suction and the filter residue is dried. By recrystallization from methylene chloride and ethyl acetate there is obtained (S)-8-chloro-11,12,13,13a-tetrahydro-N-(2-propynyl)-9H-imidazo[1,5-a]pyrrolo[2,1-c][1,4]benzodiazepine-1-carboxamide of melting point 233°–235°.

(b) 3.5 g (10 mmol) of (S)-8-chloro-11,12,13,13a-tetrahydro-N-(2-propynyl)-9H-imidazo[1,5-a]pyrrolo[2,1-c][1,4]benzodiazepine-1-carboxamide, 30 mg of mercury (II) acetate and 20 ml of glacial acetic acid are heated to reflux for 5 hours. The solution obtained is then poured into water and extracted three times with methylene chloride. The combined organic phases are dried over magnesium sulphate and evaporated. The residue is chromatographed on silica gel while eluting with methylene chloride and 10% methanol and there is obtained (S)-8-chloro-11,12,13,13a-tetrahydro-1-(5-methyl-2-oxazolyl)-9H-imidazo[1,5-a]pyrrolo[2,1-c][1,4]benzodiazepin-9-one of melting point 228°–230°.

EXAMPLE 43

9.30 g (30.2 mmol) of 1-[(5,6-dihydro-5-methyl-6-oxo-4H-imidazo[1,5-a][1,4]benzodiazepin-3-yl)carbonyl]imidazole are suspended in 60 ml of N,N-dimethylformamide and the suspension is treated with 3.0 g (40.5 mmol) of acetamidoxime. After stirring at 60° for 5.5 hours the mixture is evaporated to dryness, 70 ml of glacial acetic acid are added to the residue and the solution is heated to 120° for 2.5 hours. The solution is then evaporated and the residue is partitioned between methylene chloride and saturated sodium bicarbonate solution. The organic phase is separated, dried over magnesium sulphate and evaporated. By recrystallization of the residue from methylene chloride and ethyl acetate there is obtained 4,5-dihydro-5-methyl-3-(3-methyl-1,2,4-oxadiazol-5-yl)-6H-imidazo[1,5-a][1,4]benzodiazepin-6-one of melting point 257°–260°.

EXAMPLE 44

A mixture of 9.77 g (39 mmol) of 5,6-dihydro-5-methyl-6-oxo-4H-imidazo[1,5-a][1,4]benzodiazepine-3-carboxylic acid, 40 ml of N,N-dimethylformamide and 6.48 g (40 mmol) of N,N'-carbonyldiimidazole is stirred at 100° for 1 hour. 4.01 g (40 mmol) of cyclopropanecarboxamidoxime are subsequently added thereto and the mixture is stirred at 100° for a further 4 hours. The mixture is then evaporated and the residue is heated to 115° for 4 hours with 100 ml of acetic acid. The solution is evaporated to dryness and the residue is partitioned between methylene chloride and saturated sodium bicarbonate solution. The organic phase is separated, dried over magnesium sulphate and evaporated. By recrystallization from methylene chloride and ethyl acetate there is obtained 3-(3-cyclopropyl-1,2,4-oxadiazol-5-yl)-4,5-dihydro-5-methyl-6H-imidazo[1,5-a][1,4]benzodiazepin-6-one of melting point 202°–203°.

EXAMPLE 45

(a) 7.10 g (19 mmol) of ethyl 7-bromo-5,6-dihydro-5-methyl-6-oxo-4H-imidazo[1,5-a][1,4]benzodiazepin-3carboxylate in 30 ml of ethanol are heated to boiling for 20 minutes with a solution of 1.13 g (28 mmol) of sodium hydroxide in 15 ml of water. The solution is thereafter neutralized with 7 ml of 4N hydrochloric acid and the ethanol is removed on a rotary evaporator. After cooling the separated solid is filtered off under suction. After drying at 85° in vacuo there is obtained 7-bromo-5,6-dihydro-5-methyl-6-oxo-4H-imidazo-[1,5-a][1,4]benzodiazepine-3-carboxylic acid.

(b) 6.2 g (18 mmol) of 7-bromo-5,6-dihydro-5-methyl-6-oxo-4H-imidazo[1,5-a][1,4]benzodiazepine-3-carboxylic acid in 90 ml of N,N-dimethylformamide are stirred at 70° for 2.5 hours with 2.92 g (18 mmol) of N,N'-carbonyldiimidazole. 1.80 g (18 mmol) of cyclopropanecarboxamidoxime are subsequently added thereto and the mixture is stirred at 100° for a further 2 hours. The solution is evaporated, the residue is treated with 70 ml of acetic acid and the mixture is stirred at 120° for 5 hours. The reaction mixture is evaporated and the residue is partitioned between methylene chloride and saturated sodium bicarbonate solution. The organic phase is dried over magnesium sulphate and evaporated. By chromatography on silica gel while eluting with ethyl acetate and recrystallization from acetonitrile there is obtained 7-bromo-4,5-dihydro-3-(3-cyclopropyl-1,2,4-oxadiazol-5yl)-5-methyl-6H-imidazo[1,5-a][1,4]benzodiazepin-6-one of melting point 187°–189°.

EXAMPLE 46

7.70 g (2.72 mmol) of (S)-11,12,13,13a-tetrahydro-9-oxo-9H-imidazo[1,5-a]pyrrolo[2,1-c][1,4]benzodiazepine-1-carboxylic acid in 40 ml of N,N-dimethylformamide are stirred at room temperature for 10 minutes and at 85° for 20 minutes with 4.41 g (27.2 mmol) of N,N'-carbonyldiimidazole. 2.72 g (27.2 mmol) of cyclopropanecarboxamidoxime are subsequently added thereto and the mixture is stirred at 110° for a further hour. After removing the N,N-dimethylformamide the residue is stirred in 30 ml of acetic acid at 120° for 4 hours. The solution is evaporated and the residue is partitioned between methylene chloride and saturated sodium bicarbonate solution. The organic phase is separated, dried over magnesium sulphate and evaporated. By recrystallization from ethyl acetate there is obtained (S)-1-(3-cyclopropyl-1,2,4-oxadiazol-5-yl)-11,12,13,13a-tetrahydro-9H-imidazo[1,5-a]pyrrolo[2,1-c][1,4]benzodiazepin-9-one of melting point 211°–212°.

EXAMPLE 47

2.20 g (7 mmol of (R,S)-8-chloro-11,13a-dihydro-9-oxo-9H-imidazo[1,5-a]pyrrolo[2,1-c][1,4]benzodiazepine-1-carboxylic acid, 30 ml of N,N-dimethylformamide and 1.14 g (7 mmol) of N,N'-carbonyldiimidazole are stirred at room temperature for 10 minutes and at 65° for 1 hour. 0.70 g (7 mmol) of cyclopropanecarboxamidoxime is subsequently added thereto and the mixture is stirred at 80° for a further 2 hours. The solution is evaporated and the residue is treated with 25 ml of acetic acid. After stirring at 120° for 3 hours the reaction mixture is evaporated to dryness and the residue is partitioned between methylene chloride and saturated sodium bicarbonate solution. The organic phase is separated and dried over magnesium sulphate. By recrystallization from ethyl acetate there is obtained (R,S)-8-chloro-1-(3-cyclopropyl-1,2,4-oxadiazol-5-yl)-11,13a-dihydro-9H-imidazo[1,5-a]pyrrolo[2,1-c][1,4]benzodiazepin-9-one of melting point 250°–252°.

EXAMPLE 48

A susupension of 10.18 g (40.6 mmol) of (S)-6-chloro-1,2,3-11a-tetrahydro-5H-pyrrolo[2,1-c][1,4]benzodiazepine-5,11(10H)-dione in 35 ml of dry N,N-dimethylformamide is treated at −20° to −30° while stirring with 1.77 g (40.6 mmol) of sodium hydride (55 percent oil dispersion), the mixture is stirred at the above temperature for a further 30 minutes and there is subsequently added dropwise thereto at −70° a solution of 10.74 g (40.6 mmol) of phosphoric acid diphenyl ester chloride in 8 ml of dry N,N-dimethylformamide. After stirring in an acetone/dry-ice bath for 20 minutes there is added dropwise thereto at −70° to −55° a solution of 5 g (40.6 mmol) of 2-isocyanomethylthiophene in 5 ml of dry N,N-dimethylformamide and subsequently a solution of 4.56 g (40.6 mmol) of potassium tert.-butylate in 12 ml of dry N,N-dimethylformamide. The mixture is left to warm to room temperature, neutralized with 2.5 ml of glacial acetic acid, poured into 300 ml of water and extracted three times with methylene chloride. The organic extracts are washed four times with water, dried over magnesium sulphate and evaporated. By chromatography on silica gel while eluting with ethyl acetate and recrystallization from acetonitrile there is obtained (S)-8-chloro-11,12,13,13a-tetrahydro-1-(2-thienyl)-9H-imidazo[1,5-a]pyrrolo[2,1-c][1,4]benzodiazepin-9-one of melting point 226°–227°.

EXAMPLE 49

A suspension of 9.12 g (40.6 mmol) of 6-chloro-3,4-dihydro-4-methyl-2H-1,4-benzodiazepine-2,5(1H)-dione in 35 ml of dry N,N-dimethylformamide is treated at −20° to −30° while stirring with 1.77 g (40.6 mmol) of sodium hydride (55 percent oil dispersion), the mixture is stirred at the above temperature for a further 30 minutes and there is subsequently added dropwise thereto at −70° a solution of 10.74 g (40.6 mmol) of phosphoric acid diphenyl ester chloride in 8 ml of dry N,N-dimethylformamide. After stirring in an acetone/dry-ice bath for 20 minutes there is added dropwise thereto at −70° to −55° a solution of 5 g (40.6 mmol) of 2-isocyanomethylthiophene in 5 ml of dry N,N-dimethylformamide and subsequently a solution of 4.56 g (40.6 mmol) of potassium tert.-butylate in 12 ml of dry N,N-dimethylformamide. The mixture is left to warm to room temperature, neutralized with 2.5 ml of glacial acetic acid, poured into 300 ml of water and extracted three times with methylene chloride. The organic extracts are washed four times with water, dried over magnesium sulphate and evaporated. The residue is chromatographed on silica gel while eluting with ethyl acetate. By recrystallization from acetonitrile there is obtained 7-chloro-4,5-dihydro-5-methyl-3-(2-thienyl)-6H-imidazo[1,5-a][1,4]benzodiazepin-6-one of melting point 222°–223°.

EXAMPLE 50

(a) 18.0 g (64.8 mmol) of 7-chloro-4,5-dihydro-3-hydroxymethyl-5methyl-6H-imidazo[1,5-a][1,4]benzodiazepin-6-one, 75 g of manganese dioxide and 700 ml of methylene chloride are stirred at room temperature for 1.5 hours. The reaction mixture is filtered and the filtrate is evaporated. By recrystallization of the residue from alcohol there is obtained 7-chloro-5,6-dihydro-5-methyl-6-oxo-4H-imidazo[1,5-a][1,4]benzodiazepine-3-carboxaldehyde of melting point 204°–205°.

(b) A suspension of 5.51 g (20 mmol) of 7-chloro-5,6-dihydro-5-methyl-6-oxo-4H-imidazo[1,5-a][1,4]benzodiazepine-3-carboxaldehyde, 2.23 g (26.6 mmol) of O-methylhydroxylamine hydrochloride and 75 ml of water is treated dropwise at room temperature with a solution of 7.67 g (26.6 mmol) of sodium bicarbonate in 65 ml of water. 40 ml of methanol are added thereto and the mixture is stirred at 70° for 8 hours. The mixture is then poured into 700 ml of water, the suspension is suction filtered and the filter residue is dissolved in methylene chloride. The solution is dried over magnesium sulphate and evaporated. By chromatography on silica gel while eluting with ethyl acetate and recrystallization from ethyl acetate there is obtained 7-chloro-5,6-dihydro-5-methyl-6-oxo-4H-imidazo[1,5-a][1,4]benzodiazepine-3carboxaldehyde O-methyl oxime of melting point 173°–174°.

EXAMPLE 51

A mixture of 6.50 g (20 mmol) of 1-[[8-fluoro-5,6-dihydro-5-methyl-6-oxo-4H-imidazo[1,5-a][1,4]benzodiazepin-3-yl]carbonyl]imidazole, 50 ml of N,N-dimethylformamide and 2.10 g (20 mmol) of methoxyacetamidoxime is stirred at 100° overnight. After evaporation of the solvent the residue is dissolved in methylene chloride and washed with water. The organic solution is dried over magnesium sulphate and evaporated. By chromatography of the residue on silica gel while eluting with ethyl acetate and recrystallization from methylene chloride and ethyl acetate there is obtained 8-fluoro-4,5-dihydro-3-(3-methoxymethyl-1,2,4-oxadiazol-5-yl)-5-methyl-6H-imidazo[1,5-a][1,4]benzodiazepin-6-one of melting point 192°–194°.

EXAMPLE 52

A mixture of 6.80 g (20 mmol) of 1-[[7-chloro-5,6-dihydro-5-methyl-6-oxo-4H-imidazo[1,5-a][1,4]benzodiazepin-3-yl]carbonyl]imidazole, 50 ml of N,N-dimethylformamide and 2.10 g (20 mmol) of methoxyacetamidoxime is stirred at 100° overnight. The solution is then evaporated and the residue is partitioned between methylene chloride and water. The organic phase is dried over magnesium sulphate and evaporated. By chromatography of the residue on silica gel while eluting with ethyl acetate and recrystallization from methylene chloride and ethyl acetate there is obtained 7-chloro-4,5-dihydro-3-(3-methoxymethyl-1,2,4-oxadiazol-5-yl)-5-methyl-6H-imidazo[1,5-a][1,4]benzodiazepin-6-one of melting point 213°–215°.

EXAMPLE 53

6.80 g (20 mmol) of 1-[[7-chloro-5,6-dihydro-5-methyl-6-oxo-4H-imidazo[1,5-a][1,4]benzodiazepin-3-yl]carbonyl]imidazole, 50 ml of N,N-dimethylformamide and 3.2 g (20 mmol) of heptanecarboxamidoxime are stirred at 100° overnight. The solution is then evaporated and the residue is dissolved in methylene chloride. The organic solution is washed with water and the solvent is evaporated. By chromatography of the residue on silica gel while eluting with ethyl acetate and subsequent recrystallization from ethyl acetate there is obtained 7-chloro-3-(3-heptyl-1,2,4-oxadiazol-5-yl)-4,5-dihydro-5-methyl-6H-imidazo[1,5-a][1,4]benzodiazepin-6-one of melting point 108°–110°.

EXAMPLE 54

9.93 g (27 mmol) of 1-[[(S)-8-chloro-11,12,13,13a-tetrahydro-9-oxo-9H-imidazo[1,5-a]pyrrolo[2,1-c][1,4]benzodiazepin-1-yl]carbonyl]imidazole, 40 ml of N,N-dimethylformamide and 350 g (30.7 mmol) of cyclobutanecarboxamidoxime are stirred at 90° for 2 hours. The solvent is then evaporated and replaced by acetic acid. After stirring at 120° for 2 hours the solution is concentrated to dryness and the residue is partitioned between methylene chloride and saturated sodium bicarbonate solution. The organic phase is separated, dried over magnesium sulphate and evaporated. By chromatography on silica gel while eluting with ethyl acetate there is obtained (S)-8-chloro-1-(3-cyclobutyl-1,2,4-oxadiazol-5-yl)-11,12,13,13a-tetrahydro-9H-imidazo[1,5-a]pyrrolo[2,1-c][1,4]benzodiazepin-9-one of melting point 183°–185°.

EXAMPLE 55

5.50 g (19 mmol) of (S)-10,11,12,12a-tetrahydro-8-oxo-8H-imidazo[1,5-a]pyrrolo[2,1-c]thieno[2,3-f][1,4]diazepine-1-carboxylic acid, 30 ml of N,N-dimethylformamide and 3.08 g (19 mmol) of N,N'-carbonyldiimidazole are stirred at room temperature for 1 hour. 1.40 g (19 mmol) of acetamidoxime are subsequently added thereto and the mixture is stirred at 70° for a further 2 hours. The mixture is poured into 400 ml of water, stirred for 20 minutes, suction filtered and the filter residue is dried. 4.49 g of the thus-obtained product are stirred in 40 ml of glacial acetic acid at 110° for 1.5 hours. The solution is evaporated and the residue is partition between methylene chloride and saturated sodium bicarbonate solution. The organic phase is separated, dried over magnesium sulphate and concentrated. By recrystallization of the residue from ethyl acetate there is obtained (S)-10,11,12,12a-tetrahydro-1-(3-methyl-1,2,4-oxadiazol-5-yl)-8H-imidazo[1,5-a]pyrrolo[2,1-c]thieno[2,3-f]diazepin-8-one of melting point 166°–167°.

EXAMPLE 56

(a) 9.60 g (30 mmol) of ethyl 7-chloro-5,6-dihydro-5-methyl-6-oxo-4H-imidazo[1,5-a][1,4]benzodiazepine-3-carboxylate are heated to reflux for 2 hours with 20 ml of hydrazine hydrate in 50 ml of ethanol. The mixture is concentrated to about 30 ml and the residue is diluted with water. The suspension is suction filtered and there is obtained 7-chloro-5,6-dihydro-5-methyl-6-oxo-4H-imidazo[1,5-a][1,4]benzodiazepine-3-carboxyhydrazide of melting point 288°–290°.

(b) 9.0 g (33.3 mmol) of 7-chloro-5,6-dihydro-5-methyl-6-oxo-4H-imidazo[1,5-a][1,4]benzodiazepine-3-carboxyhydrazide are heated to boiling under reflux for 1 hour together with 62 ml (339 mmol) of triethyl orthoacetate in 250 ml of ethanol. The mixture is then concentrated to about 70 ml, diluted with 100 ml of ethyl acetate and cooled in an ice-bath. By filtering off the precipitated product under suction and washing with ethyl acetate there is obtained N'-[(E/Z)-1-ethoxyethylidene]-7-chloro-5,6-dihydro-5-methyl-6-oxo-4H-imidazo[1,5-a][1,4]benzodiazepine-3-carboxyhydrazide of melting point 244°–245°.

(c) 3.50 g (25.3 mmol) of N'-[(E/Z)-1-ethoxyethylidene]-7-chloro-5,6-dihydro-5-methyl-6-oxo-4H-imidazo[1,5-a][1,4]benzodiazepine-3-carboxyhydrazide in 30 ml of n-butanol are heated to boiling under reflux overnight with 6 ml of 1,8-diazabicyclo[5.4.0]undec-7-ene. After evaporation of the solvent the residue is dissolved in methylene chloride and the solution is washed twice with water. The organic phase is dried over magnesium sulphate and evaporated. By chromatography of the residue on silica gel while eluting with methylene chloride and 5% methanol and recrystallization from methylene chloride and ethyl acetate there is obtained 7-chloro-5,6-dihydro-3-(5-methyl-1,3,4-oxadiazol-2-yl)-5-methyl-6H-imidazo[1,5-a][1,4]benzodiazepin-6-one of melting point 254°–255°.

EXAMPLE 57

A mixture of 11.0 g (30 mmol) of 1-[[(S)-8-chloro-11,12,13,13a-tetrahydro-9-oxo-9H-imidazo[1,5-a]pyrrolo[2,1-c][1,4]benzodiazepin-1-yl]carbonyl]imidazole, 50 ml of N,N-dimethylformamide and 4.35 g (34 mmol) of cyclopentanecarboxamidoxime is stirred at 85° for 3 hours. The solvent is then evaporated and the residue is heated to 115° for 1.5 hours with 50 ml of acetic acid. The mixture is evaporated and the residue is partitioned between methylene chloride and saturated sodium bicarbonate solution. The organic phase is separated, dried over magnesium sulphate and evaporated. By recrystallization from ethyl acetate and hexane there is obtained (S)-8-chloro-1-(3-cyclopentyl-1,2,4-oxadiazol-5-yl)-11,12,13,13a-tetrahydro-9H-imidazo[1,5-a]pyrrolo[2,1-c][1,4]benzodiazepin-9-one of melting point 177°–178°.

EXAMPLE 58

(a) 6.4 g of 3,4-dihydro-4-methyl-2-H-thieno[3,2-e][1,4]diazepine-2,5(1H)-dione are suspended in 640 ml of chloroform. There are added successively thereto 47.6 ml of N,N-dimethyl-p-toluidine and 9.45 ml of phosphorus oxychloride and the mixture is heated to reflux temperature for 15 hours while stirring. The reaction mixture is then cooled and stirred intensively for 30 minutes with 1 l of saturated aqueous sodium hydrogen carbonate solution. The organic phase is separated and the aqueous phase is extracted twice with chloroform. The chloroform extracts are dried with sodium sulphate and the solvent is distilled off in vacuo. The residue contains crude 2-chloro-3,4-dihydro-4-methyl-2H-thieno[3,2-e][1,4]diazepin-5(5H)-one mixed with N,N-dimethyl-p-toluidine.

A solution of the potassium salt of tert.-butyl isocyanoacetate is prepared by the dropwise addition of a solution of 9.2 g of tert.-butyl isocyanoacetate in 20 ml of dimethylformamide at −10° to −5° to a solution of 7.24 g of potassium tert.-butoxide in 250 ml of dimethylformamide. To this solution is added dropwise at −10° the above-described mixture of crude 2-chloro-3,4-dihydro-4-methyl-2H-thieno[3,2-e][1,4]diazepin-5(5H)-one and N,N-dimethyl-p-toluidine. The mixture is stirred at −5° for a further 30 minutes and at room temperature for 2 hours. The reaction mixture is then treated at 0° with 4.9 ml of glacial acetic acid and poured into 5 l of saturated aqueous sodium hydrogen carbonate solution. The mixture is extracted three times with ethyl acetate and twice with chloroform. The organic phases are washed with saturated sodium chloride solution and dried over sodium sulphate. The solvent and the majority of the N,N-dimethyl-p-toluidine are distilled off in a high vacuum. The residue is chromatographed through silica gel. Using a mixture of chloroform and ethanol (98.8:1.2) there is eluted tert.-butyl 5,6-dihydro-5-methyl-6-oxo-4H-imidazo[1,5-a]thieno[2,3-f][1,4]diazepine-3-carboxylate. The residue from the eluate is crystallized from ethyl acetate and diisopropyl ether. There are obtained colourless crystals of t-butyl 5,6-dihydro-5-methyl-6-oxo-4H-imidazo[1,5-a]thieno[2,3-f][1,4]diazepine-3-carboxylate of melting point 178°–179°.

(b) 7.2 g of tert.butyl 5,6-dihydro-5-methyl-6-oxo-4H-imidazo[1,5-a]thieno[2,3-f][1,4]diazepine-3-carboxylate are dissolved in 100 ml of trifluoroacetic acid while cooling with ice and left to stand at room temperature for 90 minutes. The solution is then evaporated in vacuo and the residue is crystallized from ethyl acetate and diethyl ether. There are obtained 6.65 g of crude 5,6-dihydro-5-methyl-6-oxo-4H-imidazo[1,5-a]thieno[2,3-f][1,4]diazepine-3-carboxylic acid.

(c) 6.65 g of 5,6-dihydro--5-methyl-6-oxo-4H-imidazo[1,5-a]thieno[2,3-f][1,4]diazepine-3-carboxylic acid are suspended in 200 ml of dimethylformamide. 4.6 g of carbonyldiimidazole are added thereto while stirring and the mixture is stirred at room temperature for 75 minutes. 3.0 g of cyclopropanecarboxamidoxime are then added thereto and the mixture is heated while stirring to 80° for 13 hours and to 120° for 2.5 hours. The reaction mixture is poured into 4 l of saturated aqueous sodium hydrogen carbonate solution and extracted three times with 800 ml of ethyl acetate each time. The organic extracts are washed with saturated sodium chloride solution, dried over sodium sulphate and evaporated in vacuo. The residue is chromatographed through silica gel. Using a mixture of chloroform and ethanol (99.4:0.6) there is eluted 3-(3-cyclopropyl-1,2,4-oxadiazol-5-yl)-5,6-dihydro-5-methyl-4H-imidazo[1,5-a]thieno[2,3-f][1,4]diazepin-6-one. This is recrystallized from ethyl acetate, m.p. 204°–205°.

EXAMPLE 59

(a) 44.3 g of cyanoacetic acid and 59.2 g of sarcosine ethyl ester are dissolved successively in 1.4 l of dichloromethane. A solution of 114 g of dicyclohexyl carbodiimide in 1.1 l of dichloromethane is added dropwise within 15 minutes at 15° to 20°. Stirring is continued for 1 hour at room temperature and for 30 minutes at 5°. The precipitated dicyclohexyl urea is filtered off and the filtrate is evaporated in a vacuum. The residue is dissolved in toluene and chromatographed through silica gel. Using a mixture of toluene and ethyl acetate (2:1) there is eluted oily N-(cyanoacetyl)sarcosine ethyl ester.

(b) 74.5 g of N-(cyanoacetyl)sarcosine ethyl ester are added to a suspension of 30.7 g of 2,5-dihydroxy-1,4-dithiane in 600 ml of ethanol. The resulting suspension is heated to 50° whereupon a mixture of 10 ml of piperidine and 20 ml of triethylamine is added dropwise. The resulting mixture is stirred at 75° for 2¼ hours. A small amount of insoluble material is filtered off and the filtrate is evaporated in a vacuum. The residue is dissolved in chloroform which contains 2% of ethanol and chromatographed through silica gel. Using a mixture of chloroform and ethanol (98:2) there is eluted crude 3,4-dihydro-4-methyl-2H-thieno[2,3-e][1,4]diazepine-2,5(1H)-dione. By boiling in a mixture of toluene and chloroform there are obtained crystals of melting point 235°–238°. A sample is recrystallized from ethanol, m.p. 238°–239°.

(c) From 8.0 g of 3,4-dihydro-4-methyl-2H-thieno[2,3-e][1,4]diazepine-2,5(1H)-dione and by a procedure analogous to that described in Example 58(a) there is obtained tert.butyl 5,6-dihydro-5-methyl-4-oxo-4H-imidazo[1,5-a]thieno[3,2-f][1,4]diazepine-7-carboxylate of melting point 199°–200° (after recrystallization from diethyl ether/diisopropyl ether).

(d) From 6.1 g of tert.butyl 5,6-dihydro-5-methyl-4-oxo-4H-imidazo[1,5-a]thieno[3,2-f][1,4]diazepine 7-carboxylate and by a procedure analogous to that described in Example 58(b) there is obtained 5,6-dihydro-5-methyl-4-oxo-4H-imidazo[1,5-a]thieno[3,2-f][1,4]diazepine-7-carboxylic acid of melting point (decomposition) 262°–263° (after recrystallization from ethyl acetate).

(e) From 4.9 g of 5,6-dihydro-5-methyl-4-oxo-4H-imidazo[1,5-a]thieno[3,2-f][1,4]diazepine-7-carboxylic acid and by a procedure analogous to that described in Example 58(c) there is obtained 7-(3-cyclopropyl-1,2,4-oxadiazol-5-yl)-5,6-dihydro-4H-imidazo[1,5-a]thieno[3,2-f][1,4]diazepin-4-one of melting point 194°–195° (after recrystallization from ethyl acetate/diisopropyl ether).

(S)-8-Chloro-11,12,13,13a-tetrahydro-1-(3-methyl-1,2,4-oxadiazol-5-yl)-9H-imidazo[1,5-a]pyrrolo[2,1-c][1,4]benzodiazepin-9-one can be used as the active substance for the manufacture of pharmaceutical preparations as indicated in Examples A and B hereinafter:

EXAMPLE A

Tablets of the following composition can be manufactured in the usual manner:

|  | mg/tablet |
| --- | --- |
| Active substance | 0.2 |
| Lactose | 140 |
| Maize starch | 50.8 |
| Polyvinylpyrrolidine | 8 |
| Magnesium stearate | 1 |
| Tablet weight | 200 |

EXAMPLE B

Capsules of the following composition can be manufactured in the usual manner:

|  | mg/capsule |
| --- | --- |
| Active substance | 0.5 |
| Lactose | 40 |
| Maize starch | 8 |
| Talc | 1 |
| Magnesium stearate | 0.5 |
| Capsule fill weight | 50 |

The compounds of formula I listed hereinafter can be used as the active substance in the above Examples A and B in place of (S)-8-chloro-11,12,13,13a-tetrahydro-1-(3-methyl-1,2,4-oxadiazol-5-yl)-9H-imidazo[1,5-a]pyrrolo[2,1-c][1,4]benzodiazepin-9-one:

(S)-8-Chloro-7-fluoro-11,12,13,13a -tetrahydro-1-(3-methyl-1,2,4-oxadiazol-5-yl)-9H-imidazo[1,5-a]pyrrolo[2,1-c][1,4]benzodiazepin-9-one, (S)-8-bromo-11,12,13,13a -tetrahydro-1-(3-methyl-1,2,4-oxadiazol-5-yl)-9H-imidazo[1,5-a]pyrrolo[2,1-c][1,4]benzodiazepin-9-one, (S)-8-chloro-12,12a-dihydro-1-(3-methyl-1,2,4-oxadiazol-5-yl)-9H,11H-azeto[2,1-c]imidazo[1,5-a][1,4]benzodiazepin-9-one, (S)-12,12a-dihydro-1-(3-methyl-1,2,4-oxadiazol-5-yl)-8-(trifluoromethyl)-9H,11H-azeto[2,1-c]imidazo[1,5-a][1,4]benzodiazepin-9-one, 7-chloro-3-(3-cyclopropyl-1,2,4-oxadiazol-5-yl)-5,6-dihydro-5-methyl-4H-imidazo[1,5-a][1,4]benzodiazepin-6-one, (S)-8-chloro-1-(3-cyclopropyl-1,2,4-oxadiazol-5-yl)-12,12a-dihydro-9H,11H-azeto[2,1-c]imidazo[1,5-a][1,4]benzodiazepin-9-one, (S)-8-chloro-1-(3-cyclopropyl-1,2,4-oxadiazol-5-yl)-11,12,13,13a-tetrahydro-9H-imidazo[1,5-a]pyrrolo[2,1-c][1,4]benzodiazepin-9-one and 3-(3-cyclopropyl-1,2,4-oxadiazol-5-yl)-8-fluoro-5,6-dihydro-5-methyl-4H-imidazo[1,5-a][1,4]benzodiazepin-6-one.

What is claimed:

1. A compound of the formula:

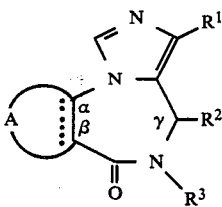

wherein A together with the two carbon atoms denoted by α and β is one of the groups

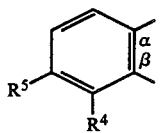 (1)

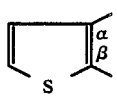 (2)

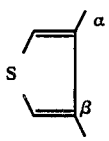 (3)

and

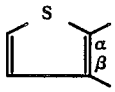 (4)

and the dotted line signifies the double bond present in cases (1), (2) and (4) and wherein $R^1$ signifies a 5- or 6-membered aromatic heterocyclic group selected from the group consisting of 2-oxazolyl, 4-oxazolyl, 5-oxazolyl, 3-isoxazolyl, 4-isoxazolyl, 5-isoxazolyl, 2-thiazolyl, 2-imidazolyl, 4-imidazolyl, 1,2,4-oxadiazol-3-yl, 1,2,4-oxadiazol-5-yl, 1,3,4-oxadiazol-2-yl, 1,2,5-oxadiazol-3-yl, 1,2,4-thiadiazol-3-yl, 1,3,4-thiadiazol-2-yl, 1,2,5-thiadiazol-3-yl, 1,2,4-triazol-3-yl, 1,2,4-triazol-5-yl, 2-furyl, 2-thienyl, 1-pyrrolyl, 1-imidazolyl, 1-pyrazolyl, 1,3,4-triazol-1-yl, 2-pyrimidinyl, 4-pyrimidinyl, 5-pyrimidinyl, 2-pyrazinyl, 4-pyridazinyl, 1,2,4-triazin-3-yl, 1,2,4-triazin-5-yl and 1,2,4-triazin-6-yl, which optionally may be substituted on a carbon atom by lower alkyl, $(C_3-C_6)$-cycloalkyl, trifluoromethyl, phenyl, amino, lower alkylamino, lower alkoxy-lower alkyl or hydroxy, a keto-enol tautomerism being possible in the case of groups which are substituted by hydroxy or the group —$C(R^6)$=$NOR^7$, $R^2$ signifies hydrogen and $R^3$ signifies hydrogen or lower alkyl or $R^2$ and $R^3$ together signify dimethylene, trimethylene or propenylene, $R_4$ and $R^5$ each signify hydrogen, halogen, trifluoromethyl, cyano, nitro, amino or lower alkyl, $R^6$ signifies hydrogen or lower alkyl and $R^7$ signifies lower alkyl, the compounds of formula I having the (S) or (R,S) configuration with reference to the carbon a atom denoted by γ when $R^2$ and $R^3$ together signify dimethylene, trimethylene or propenylene; provided that $R^1$ is not 1,2,4-oxadiazol-5-yl, 1,2,4-oxadiazol-3-yl, 1,3,4-oxadiazol-2-yl or 1,2,5-oxadiazol-3-yl which is unsubstituted or substituted by lower alkyl, when A signifies the group (1), $R^2$ signifies hydrogen, $R^3$ signifies hydrogen or methyl, and one of $R_4$ and $R^5$ signifies hydrogen and the other signifies hydrogen, halogen or nitro or pharmaceutically acceptable acid addition salts thereof.

2. A compound in accordance with claim 1 wherein A signifies the group (1) and the heterocyclic group is unsubstituted or substituted on a carbon atom by lower alkyl, trifluoromethyl, phenyl, amino, lower alkylamino or hydroxy.

3. A compound in accordance with claim 1 wherein A signifies the group (1) and the heterocyclic group is substituted on a carbon atom by $(C_3-C_6)$-cycloalkyl or lower alkoxy-lower alkyl.

4. A compound in accordance with claim 1, wherein $R^1$ signifies the group —$C(R^6)$=$NOR^7$ or a 5-membered, aromatic heterocyclic group selected form the group consisting of 2-oxazolyl, 4-oxazolyl, 5-oxazolyl, 3-isoxazolyl, 4-isoxazolyl, 5-isoxazolyl, 2-thiazolyl, 1,2,4-oxadiazol-3-yl, 1,2,4-oxadiazol-5-yl, 1,34,-oxadiazol-2-yl, 1,2,5-oxadiazol-3-yl, 1,2,4-thiadiazol-yl, 1,3,4-thiadiazol-2-yl and 1,2,5-thiadiazol-3-yl, and which is optionally substituted by $(C_3-C_6)$-cycloalkyl or trifluoromethyl, $R^5$ signifies hydrogen or lower alkyl and $R^7$ signifies lower alkyl.

5. A compound in accordance with claim 4, wherein $R^6$ signifies hydrogen or the heterocyclic group is attached via a carbon atom adjacent to two hetero atoms.

6. A compound in accordance with claim 4, wherein $R^1$ signifies a 1,2,4-oxadiazol-3-yl, 1,2,4-oxadiazol-5-yl or 1,3,4-oxadiazol-2-yl group which is optionally substituted by $(C_3-C_6)$-cycloalkyl.

7. A compound in accordance with claim 6, wherein $R^1$ signifies 3-cyclopropyl-1,2,4-oxadiazol-5-yl.

8. A compound in accordance with claim 7 wherein $R^2$ signifies hydrogen and $R^3$ signifies lower alkyl or $R^2$ and $R^3$ together signify dimethylene or trimethylene and wherein they have the (S) configuration with respect to the carbon atom denoted by γ when $R^2$ and $R^3$ together signify dimethylene or trimethylene.

9. A compound in accordance with claim 8, wherein A signifies the group (1), $R^4$ signifies hydrogen, halogen or trifluoromethyl and $R^5$ signifies hydrogen or halogen.

10. The compound; 7-chloro-3-(3-cyclopropyl-1,2,4-oxadiazol-5-yl-5,6-dihydro-methyl-4H-imidazo[1,5-a][1,4]benzodiazepin-6-one.

11. The compound; (S)-8-chloro-7-fluoro-11,12,13,13a-tetrahydro-1-(3-methyl-1,2,4-oxadiazol-5-yl)-9H-imidazo[1,5-a]pyrrolo-[2,1-c]-[1,4]benzodiazepin-9-one.

12. The compound; (S)-8-bromo-11,12,13,13a-tetrahydro-1-(3-methyl-1,2,4-oxadiazol-5-yl)-9H-imidazo[1,5-a]pyrrolo[2,1-c]-[1,4]benzodiazepin-9-one.

13. The compound; (S)-8-chloro-11,12,13,13a-tetrahydro-1-(3-methyl-,2,4-oxadiazol-yl)-9H-imidazo[1,5-a]pyrrolo[2,1-c][1,4]benzodiazepin-one.

14. The compound; (S)-8-chloro-12,12a-dihydro-1-(3-methyl-1,2,4-oxadiazol-5-yl)-9H,11H-azeto[2,1-c]imidazo[1,5-a][1,4]benzodiazepin-9-one.

15. The compound; (S)-12,12a-dihydro-1-(3-methyl-1,2,4-oxadiazol-5-yl)-8-(   )trifluoromethyl)-9H,11H-azeto[2,1-c]imidazo[1,5-a][1,4]benzodiazepin-9-one.

16. The compound; (S)-8-chloro-1-(3-cylcopropyl-1,2,4oxadiazol-5-yl)-12,12a-dihydro-H,11H-azeto-[2,1-c]imidazo[1,5-a][1,4]benzodiazepin-9-one.

17. The compound; (S)-8-chloro-1-(3-cyclopropyl-,2,4oxadiazol-5-yl)-11,12,13,13a-tetrahydro-9H-imidazo[1,5-a]pyrrolo[2,1-c][1,4]benzodiazepine-9-one.

18. The compound; 3-(3-cyclopropyl-1,2,4-oxadiazol-5-yl)-8-fluoro-5,6-dihydro-5-methyl-4H-imidazo[1,5-a][1,4]benzodiazepin-6-one.

19. A compound selected from the group consisting of
- (R,S)-8-chloro-12,12a-dihydro-1-(3-methyl-1,2,4-oxadiazol-5-yl)-9H,11H-azeto-[2,1-c]imidazo[1,5-a][1,4]-benzodiazepin-9-one.
- (R,S)-7-fluoro-11,12,13,13a-tetrahydro-1-(3-methyl-1,2,4-oxadiazol-5-yl)-9H-imidazo[1,5-a]pyrrolo[2,1-c][1,4]benzodiazepin-9-one,
- (S)-8-chloro-11,12,13,13a-tetrahydro-1-(5-methyl-1,2,4-oxadiazol-3-yl)-9H-imidazo[1,5-a]pyrrolo[2,1-c][1,4]benzodiazepin,
- (S)-8-chloro-11,12,13,13a-tetrahydro-1-(3-iospropyl-1,2,4-oxadiazol-5-yl)-9H-imidazo[1,5-a]pyrrolo[2,1-c][1,4]benzodiazepin-9-one,
- (R,S)-8-chloro-12,12a-dihydro-1-(5-methyl-1,3,4-oxadiazol-2-yl)-9H,11H-azeto[2,1-c]imidazo[1,5-a][1,4]benzodiazepin-9-one,
- (S)-8-chloro-12,12a-dihydro-1-(1,3,4-oxadiazol-2-yl)-9H,11H-azeto[2,1-c]imidazo[1,5-a][1,4]benzodiazepin-9-one.

20. A compound of the formula

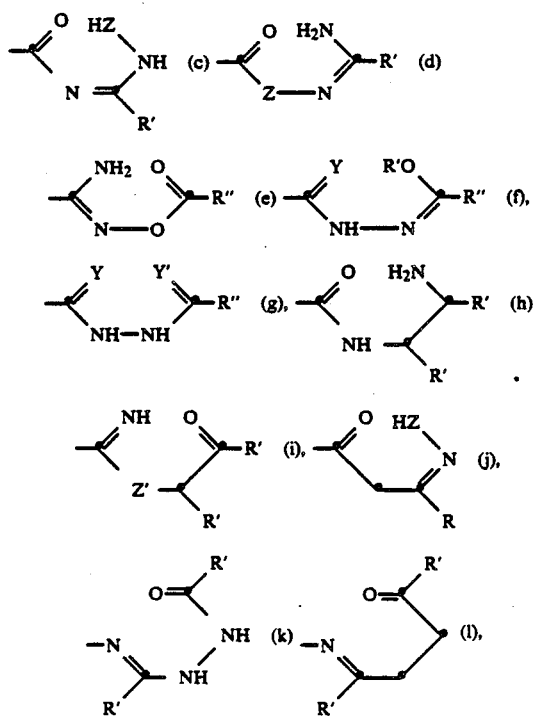

wherein Q is a group selected from

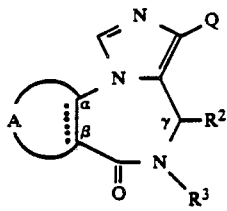

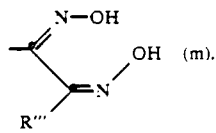

—C(NH2)=NOH, —C(=Y)—NH—NH2, —C(=Y)—NHNHC(R')=Y', —C(NH2)=Z', —CO—CH2—COR$^V$, —COCO—R''' and —CONH—N=C(-R)—COR$^V$, R$^2$ signifies hydrogen, R$^3$ signifies hydrogen or alkyl or R$^2$ and R$^3$ goether signify dimethylene, trimethylene or propenylene, A is together with the two carbon atom denoted by α and β is one of the groups

and

and the dotted line signifies the double bond present in cases (1), (2) and (4) and Y and Y' each signify an oxygen or sulphur atom, Z signifies an oxygen atom or the group —NR$^8$—, R$^8$ signifies hydrogen or lower alkyl, Z' signifies a sulphur atom or the group —NH—, R signifies hydrogen, lower alkyl, (C3-C6)-cycloalkyl, lower alkoxy-lower alkyl or hydroxy, R' signifies hydrogen, lower alkyl, (C3-C6)-cycloalkyl, lower alkoxy-lower alkyl or phenyl, R'' signifies hydrogen, lower alkyl, (C3-C6)-cycloalkyl, lower alkoxy-lower alkyl, trifluoromethyl or phenyl and R''' signifies hydrogen, lower alkyl, (C3-C6)-cycloalkyl or lower alkoxy-lower alkyl, R$^{81}$ signifies lower alkyl, R$^{IV}$ signifies lower alkyl, (C3-C6)-cycloalkyl or lower alkoxy-lower alkyl, R$^V$ signifies hydrogen, lower alkyl, (C3-C6)-cycloalkyl, lower alkoxy-lower alkyl or lower alkoxy and R$^{VI}$ signifies hydrogen, (C1-C6)-alkyl or lower alkoxy-(C1-C6)-alkyl.

21. A method of treating convulsions, anxiety states, muscle tensions, tension states and insomnia which comprises administering to a patient in need of such treatment an effective amount of a compound of the formula

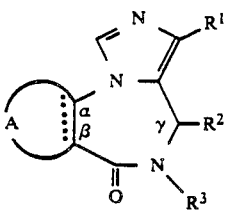

wherein A together with the two carbon atoms denoted by α and β signifies one of the groups

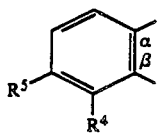 (1)

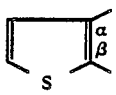 (2)

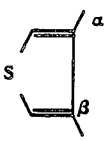 (3)

and

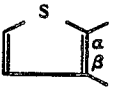 (4)

and the dotted line signifies the double bond present in cases (1), (2) and (4) and wherein $R^1$ signifies a 5- or 6-membered aromatic heterocyclic group selected form the group consisting of 2-oxazolyl, 4-oxazolyl, 5-oxazolyl, 3-isoxazolyl, 4-isoxazolyl, 5-isoxazolyl, 2-thiazolyl, 2-imidazoyl, 4-imidazolyl, 1,2,4-oxadiazol-3-yl, 1,2,4-oxadiazol-5-yl, 1,3,4-oxadiazol-2-yl, 1,2,5-oxadiazol-3-yl, 1,2,4-thiadiazol-3-yl, 1,3,4-thiadiazol-2-yl, 1,2,5-thiadiazol-3-yl, 1,2,4-triazol-3-yl, 1,2,4-triazol-5-yl, 2-furyl, 2-thienyl, 1-pyrrolyl, 1-imidazolyl, 1-pyrazolyl, 1,3,4-triazol-1-yl, 2-pyrimidinyl, 4-pyrimidinyl, 5-pyrimidinyl, 2-pyrazinyl, 4-pyridazinyl, 1,2,4-triazin-3-yl, 1,2,4-triazin-5-yl and 1,2,4-triazin-6-yl, which optionally may be substituted on a carbon a atom by lower alkyl, ($C_3$–$C_6$)-cycloalkyl, trifluoromethyl, phenyl, amino, lower alkylamino, lower alkoxy-lower alkyl or hydroxy, a keto-enol tautomerism being possible in the case of groups which are substituted by hydroxy or the group $-C(R^6)=NOR^7$, $R^2$ signifies hydrogen and $R^3$ signifies hydrogen or lower alkyl or $R^2$ and $R^3$ together signify dimethylene, trimethylene or propenylene, $R^4$ and $R^5$ each signify hydrogen, halogen, trifluoromethyl, cyano, nitro, amino or lower alkyl, $R^6$ signifies hydrogen or lower alkyl and $R^7$ signifies lower alkyl, the compounds of formula I having the (S) or (R,S) configuration with reference to the carbon a atom denoted by γ when $R^2$ and $R^3$ together signify dimethylene, trimethylene or propenylene; provided that $R^1$ is not 1,2,4-oxadiazol-5-yl, 1,2,4-oxadiazol-3-yl, 1,3,4-oxadiazol-2-yl or 1,2,5-oxadiazol-3-yl which is unsubstituted or substituted by lower alkyl, when A signifies the group (1), $R^2$ signifies hydrogen, $R^3$ signifies hydrogen or methyl, and one of $R^4$ and $R^5$ signifies hydrogen and the other signifies hydrogen, halogen or nitro or pharmaceutically acceptable acid addition salts thereof.

22. A compound in accordance w with claim 20, wherein Q signifies the group $-CON=C(CH_3)N(CH_3)_2$, $R^2$ and $R^3$ together signify dimethylene, $R^4$ signifies chlorine and $R^5$ signifies hydrogen.

23. A compound in accordance with claim 20, wherein Q signifies the group $-CON=C(CH_3)N(CH_3)_2$, $R^2$ and $R^3$ together signify trimethylene, $R^4$ signifies bromine and $R^5$ signifies fluorine.

24. A compound in accordance with claim 20, wherein Q signifies the group $-CON=C(CH_3)n(CH_3)_2$, $R^2$ and $R^3$ together signify trimethylene, $R^4$ signifies bromine and $R^5$ signifies hydrogen.

25. A compound in accordance with claim 20, wherein Q signifies the group $-CON=C(CH_3)n(CH_3)_2$, $R^2$ and $R^3$ together signify trimethylene, $R^4$ signifies chlorine and $R^5$ signifies hydrogen.

26. A compound in accordance with claim 1, 3-(3-cyclopropyl-1,2,4-oxadiazol-5-yl)-4,5-dihydro-5-methyl-6H-imidazo[1,5-a][1,4]benzodiazepin-6-one.

* * * * *